US010765434B2

(12) United States Patent
Harris et al.

(10) Patent No.: US 10,765,434 B2
(45) Date of Patent: Sep. 8, 2020

(54) BIASED-TRACK REVOLVER LOADING SURGICAL CLIP APPLIER

(71) Applicant: Ethicon LLC, Guaynabo, PR (US)

(72) Inventors: Demetrius Harris, Cincinnati, OH (US); Joshua Young, Loveland, OH (US); Sarah Worthington, Maineville, OH (US); Stephen D. Geresy, West Chester, OH (US)

(73) Assignee: Ethicon LLC, Guaynabo, PR (US)

( * ) Notice: Subject to any disclaimer, the term of this patent is extended or adjusted under 35 U.S.C. 154(b) by 233 days.

(21) Appl. No.: 15/896,496

(22) Filed: Feb. 14, 2018

(65) Prior Publication Data

US 2019/0247047 A1 Aug. 15, 2019

(51) Int. Cl.
| *A61B 17/128* | (2006.01) |
|---|---|
| *A61B 17/00* | (2006.01) |
| *A61B 17/068* | (2006.01) |
| *A61B 17/122* | (2006.01) |
| *A61B 34/30* | (2016.01) |

(52) U.S. Cl.
CPC .... *A61B 17/1285* (2013.01); *A61B 17/00234* (2013.01); *A61B 17/0682* (2013.01); *A61B 17/122* (2013.01); *A61B 2017/00327* (2013.01); *A61B 2034/302* (2016.02)

(58) Field of Classification Search
CPC ... A61B 17/0682; A61B 17/10; A61B 17/128; A61B 17/1285; A61B 2017/2926
See application file for complete search history.

(56) References Cited

U.S. PATENT DOCUMENTS

| 8,403,945 B2 | 3/2013 | Whitfield et al. |
|---|---|---|
| 9,232,979 B2 | 1/2016 | Parihar et al. |
| 2011/0224696 A1 | 9/2011 | Huitema et al. |
| 2014/0005693 A1 | 1/2014 | Shelton, IV et al. |
| 2016/0287252 A1 | 10/2016 | Parihar |

(Continued)

FOREIGN PATENT DOCUMENTS

| EP | 0419071 A3 | 3/1991 |
|---|---|---|
| EP | 1026994 A2 | 8/2000 |
| EP | 2412318 A2 | 2/2012 |

(Continued)

OTHER PUBLICATIONS

ISR/WO from PCT/IB2019/050353 (that claims priority to the present application) dated Apr. 26, 2019.

*Primary Examiner* — Melanie R Tyson
(74) *Attorney, Agent, or Firm* — Vorys, Sater, Seymour and Pease LLP

(57) ABSTRACT

An end effector for a surgical clip applier includes a body having, a clip revolver rotatably coupled within a bore of the body and containing one or more surgical clips, a torsion member constrained between the body and the clip revolver to exert rotational force on the clip revolver, and a clip advancer that is slidingly coupled within an inner bore of the clip revolver. The inner bore of the clip revolver includes a plurality of grooves in which the clip advancer may translate. The clip advancer aligns with a distal-most surgical clip as it travels within a first of the grooves. The torsion member rotates the clip revolver as the clip advancer travels distally from the first groove so that the clip advancer travels into a second groove of the grooves, such that the clip advancer is in alignment with a second distal-most surgical clip.

20 Claims, 16 Drawing Sheets

(56) References Cited

U.S. PATENT DOCUMENTS

2018/0153543 A1 6/2018 Schneider
2018/0256139 A1 9/2018 Miller

FOREIGN PATENT DOCUMENTS

| EP | 3524179 A1 | 2/2019 |
|---|---|---|
| WO | 1999022650 A2 | 5/1999 |
| WO | 2017084000 A1 | 5/2017 |

BIASED-TRACK REVOLVER LOADING SURGICAL CLIP APPLIER

BACKGROUND

Minimally invasive surgical (MIS) instruments are often preferred over traditional open surgical devices due to reduced post-operative recovery time and minimal scarring. Endoscopic surgery is one type of MIS procedure in which an elongate flexible shaft is introduced into the body of a patient through a natural orifice. Laparoscopic surgery is another type of MIS procedure in which one or more small incisions are formed in the abdomen of a patient and a trocar is inserted through the incision to form a pathway that provides access to the abdominal cavity. Through the trocar (i.e., a trocar cannula), a variety of instruments and surgical tools can be introduced into the abdominal cavity to engage and/or treat tissue in a number of ways to achieve a diagnostic or therapeutic effect.

One surgical instrument commonly used with a trocar is a surgical clip applier, which can be used to ligate blood vessels, ducts, shunts, or portions of body tissue during surgery. Traditional surgical clip appliers have a handle and an elongate shaft extending from the handle. A pair of movable opposed jaws is positioned at the end of the elongate shaft for holding and forming a surgical clip or "ligation clip" therebetween. In operation, a user (e.g., a surgeon or clinician) positions the jaws around the vessel or duct and squeezes a trigger on the handle to close the jaws and thereby collapse the surgical clip over the vessel.

More recently, however, robotic systems have been developed to assist in MIS procedures. Instead of directly engaging a surgical instrument, users are now able to manipulate and engage surgical instruments via an electronic interface communicatively coupled to a robotic manipulator. With the advances of robotic surgery, a user need not even be in the operating room with the patient during the surgery.

Robotic surgical systems are also now capable of utilizing robotically controlled clip appliers. Such clip appliers include features for robotically feeding and forming surgical clips. Advances and improvements to the methods and devices for applying surgical clips to vessels, ducts, shunts, etc. is continuously in demand to make the process more efficient and safe.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

Figure 1:
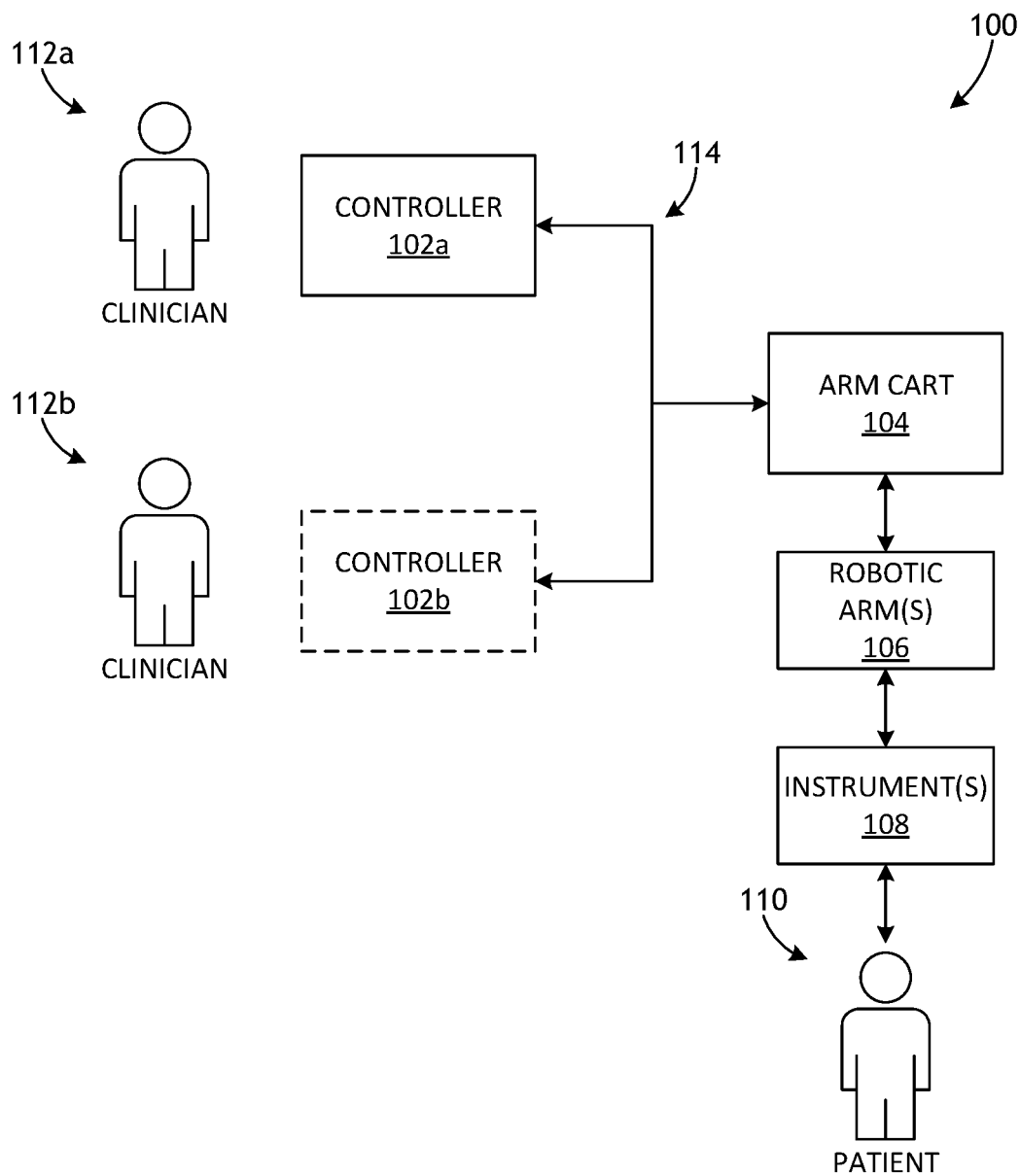
FIG. 1 is a block diagram of an example robotic surgical system that may incorporate some or all of the principles of the present disclosure.

The present disclosure is related to surgical systems and, more particularly, to surgical clip appliers with rotating clip cartridges and feeder bars that selectively feed surgical clips between opposed jaw members.

Embodiments discussed herein describe improvements to clip applier end effectors. Some end effector embodiments described herein include a body having a clip revolver that is rotatably coupled within the body near its distal end and containing one or more surgical clips. An indexer may be slidingly coupled within the body to engage the revolver and cause rotation thereof, and a feeder bar may be arranged within the body and extend through the revolver and the indexer to feed surgical clips distally. The body may include a rotation region that defines a plurality of rails, and a biasing member may be arranged within the rotation region such that the revolver is constrained between the biasing member and the rails. A first cam surface may be arranged at a distal end of the indexer and a second cam surface that corresponds with the first cam surface may be arranged at a proximal end of the revolver. In example operation, the indexer is actuated in a distal direction until the first cam surface thereof engages the second cam surface of the revolver, which pushes the revolver in a distal direction until it clears the rails within the rotation region after which the biasing member causes the revolver to rotate into position where one of the surgical clips is in alignment with the feeder bar.

Other end effector embodiments disclosed herein describe an elongate body, a revolver that holds a plurality of surgical clips, a pusher that articulates within the revolver to selectively engage each surgical clip, and a torsion member that is arranged around the revolver and secured at one end to the elongate body. The revolver may include a plurality of grooves that each align with one of the surgical clips, and the pusher may be configured to travel (traverse) within such grooves thereby constraining rotation of the revolver. The torsion member may exert a force on the revolver and thus urge rotation of the revolver. Rotation of the revolver via the torsion member may be generally inhibited when the pusher is positioned in a distal region of the grooves. However, as the pusher travels proximally, the grooves may each open into a channel that leads and connects to another of the grooves such that stored mechanical energy in the torsion member may be released to cause revolver rotation. Thus, as the pusher travels proximate to the channels, the torsion member may rotate the revolver such that the pusher travels into the channel, and then into another of the grooves to thereby index the revolver.

In contrast to conventional clip appliers, the revolver that holds the surgical clips may be arranged at a location distal to an articulable wrist joint, which helps mitigate obstructions that would otherwise impede the surgical clips having to traverse the wrist. Moreover, the presently described revolver embodiments may be configured to store surgical clips arrayed in a nested helically arrayed arrangement, which facilitates storage of a larger number of clips resulting in the tools needing to be reloaded or replaced less often during operation.

FIG. 1 is a block diagram of an example robotic surgical system 100 that may incorporate some or all of the principles of the present disclosure. As illustrated, the system 100 can include at least one master controller 102a and at least one arm cart 104. The arm cart 104 may be mechanically and/or electrically coupled to a robotic manipulator and, more particularly, to one or more robotic arms 106 or "tool drivers". Each robotic arm 106 may include and otherwise provide a location for mounting one or more surgical tools or instruments 108 for performing various surgical tasks on a patient 110. Operation of the robotic arms 106 and instruments 108 may be directed by a clinician 112a (e.g., a surgeon) from the master controller 102a.

In some embodiments, a second master controller 102b (shown in dashed lines) operated by a second clinician 112b may also direct operation of the robotic arms 106 and instruments 108 in conjunction with the first clinician 112a. In such embodiments, for example, each clinician 102a,b may control different robotic arms 106 or, in some cases, complete control of the robotic arms 106 may be passed between the clinicians 102a,b. In some embodiments, additional arm carts (not shown) having additional robotic arms (not shown) may be utilized during surgery on a patient 110, and these additional robotic arms may be controlled by one or more of the master controllers 102a,b.

The arm cart 104 and the master controllers 102a,b may be in communication with one another via a communications link 114, which may be any type of wired or wireless telecommunications means configured to carry a variety of communication signals (e.g., electrical, optical, infrared, etc.) according to any communications protocol.

The master controllers 102a,b generally include one or more physical controllers that can be grasped by the clinicians 112a,b and manipulated in space while the surgeon views the procedure via a stereo display. The physical controllers generally comprise manual input devices movable in multiple degrees of freedom, and which often include an actuatable handle for actuating the surgical instrument(s) 108, for example, for opening and closing opposing jaws, applying an electrical potential (current) to an electrode, or the like. The master controllers 102a,b can also include an optional feedback meter viewable by the clinicians 112a,b via a display to provide a visual indication of various surgical instrument metrics, such as the amount of force being applied to the surgical instrument (i.e., a cutting instrument or dynamic clamping member).

Example implementations of robotic surgical systems, such as the system 100, are disclosed in U.S. Pat. No. 7,524,320, the contents of which are incorporated herein by reference. The various particularities of such devices will not be described in detail herein beyond that which may be necessary to understand the various embodiments and forms of the various embodiments of robotic surgery apparatus, systems, and methods disclosed herein.

Figure 2:
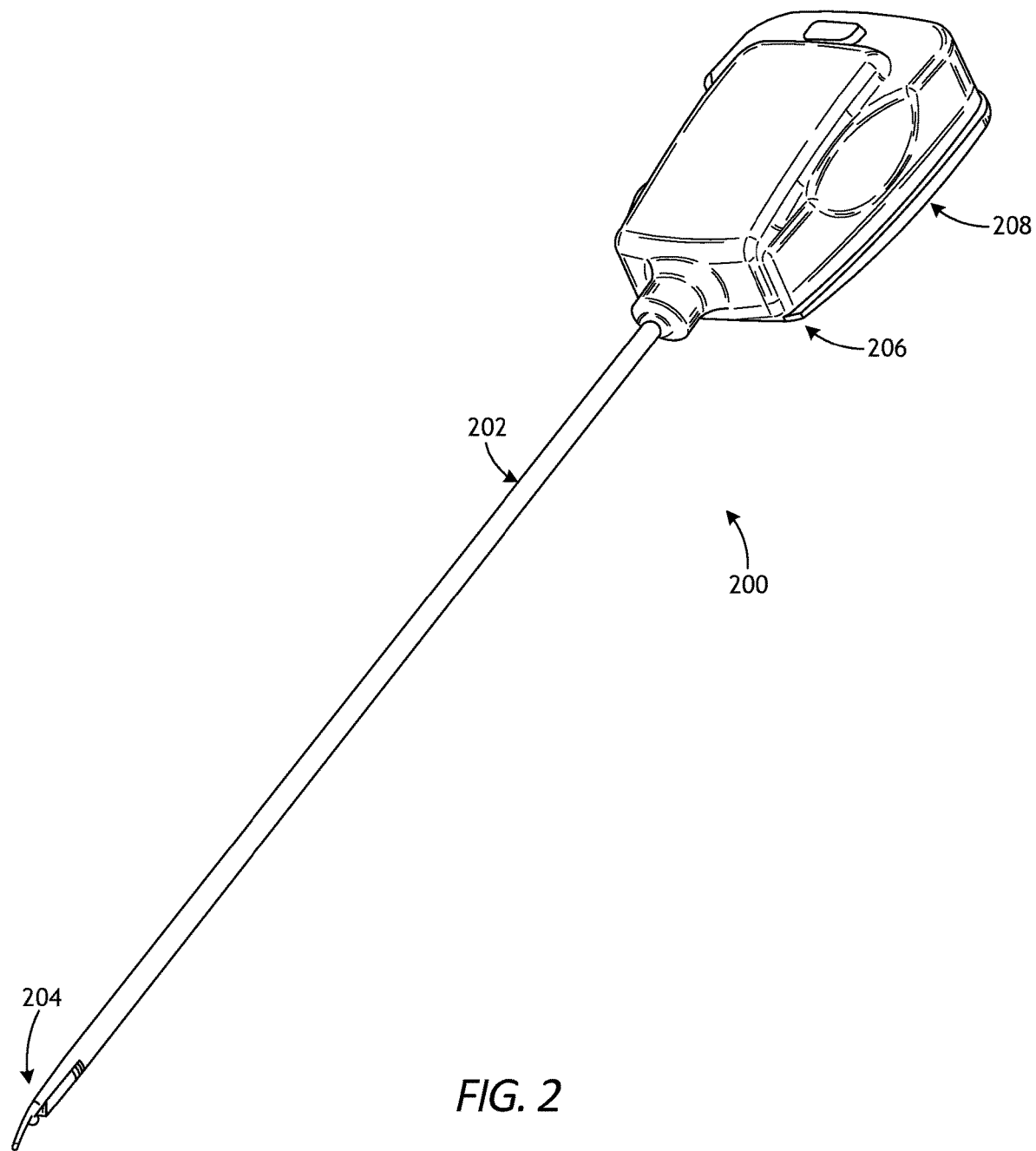
FIG. 2 is an isometric top view of an example surgical tool that may incorporate some or all of the principles of the present disclosure.

FIG. 2 is an isometric top view of an example surgical tool 200 that may incorporate some or all of the principles of the present disclosure. The surgical tool 200 may be the same as or similar to the surgical instrument(s) 108 of FIG. 1 and, therefore, may be used in conjunction with the robotic surgical system 100 of FIG. 1. Accordingly, the surgical tool 200 may be designed to be releasably coupled to a robotic arm 106 (FIG. 1) of a robotic manipulator of the robotic surgical system 100. Full detail and operational description of the surgical tool 200 is provided in U.S. Patent Pub. 2016/0287252, entitled "Clip Applier Adapted for Use with a Surgical Robot," the contents of which are hereby incorporated by reference in their entirety.

While the surgical tool 200 is described herein with reference to a robotic surgical system, it is noted that the principles of the present disclosure are equally applicable to non-robotic surgical tools or, more specifically, manually operated surgical tools. Accordingly, the discussion provided herein relating to robotic surgical systems merely encompasses one example application of the presently disclosed inventive concepts.

As illustrated, the surgical tool 200 can include an elongate shaft 202, an end effector 204 coupled to the distal end of the shaft 202, and a drive housing 206 coupled to the proximal end of the shaft 202. The terms "proximal" and "distal" are defined herein relative to a robotic surgical system having an interface configured to mechanically and electrically couple the surgical tool 200 (e.g., the drive housing 206) to a robotic manipulator. The term "proximal" refers to the position of an element closer to the robotic manipulator and the term "distal" refers to the position of an element closer to the end effector 204 and thus further away from the robotic manipulator. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

In applications where the surgical tool 200 is used in conjunction with a robotic surgical system (e.g., system 100 of FIG. 1), the drive housing 206 can include a tool mounting portion 208 designed with features that releasably couple the surgical tool 200 to a robotic arm (e.g., the robotic arms 106 or "tool drivers" of FIG. 1) of a robotic manipulator. The tool mounting portion 208 may releasably attach (couple) the drive housing 206 to a tool driver in a variety of ways, such as by clamping thereto, clipping thereto, or slidably mating therewith. In some embodiments, the tool mounting portion 208 may include an array of electrical connecting pins, which may be coupled to an electrical connection on the mounting surface of the tool driver. While the tool mounting portion 208 is described herein with reference to mechanical, electrical, and magnetic coupling elements, it should be understood that a wide variety of telemetry modalities might be used, including infrared, inductive coupling, or the like.

Figure 3:
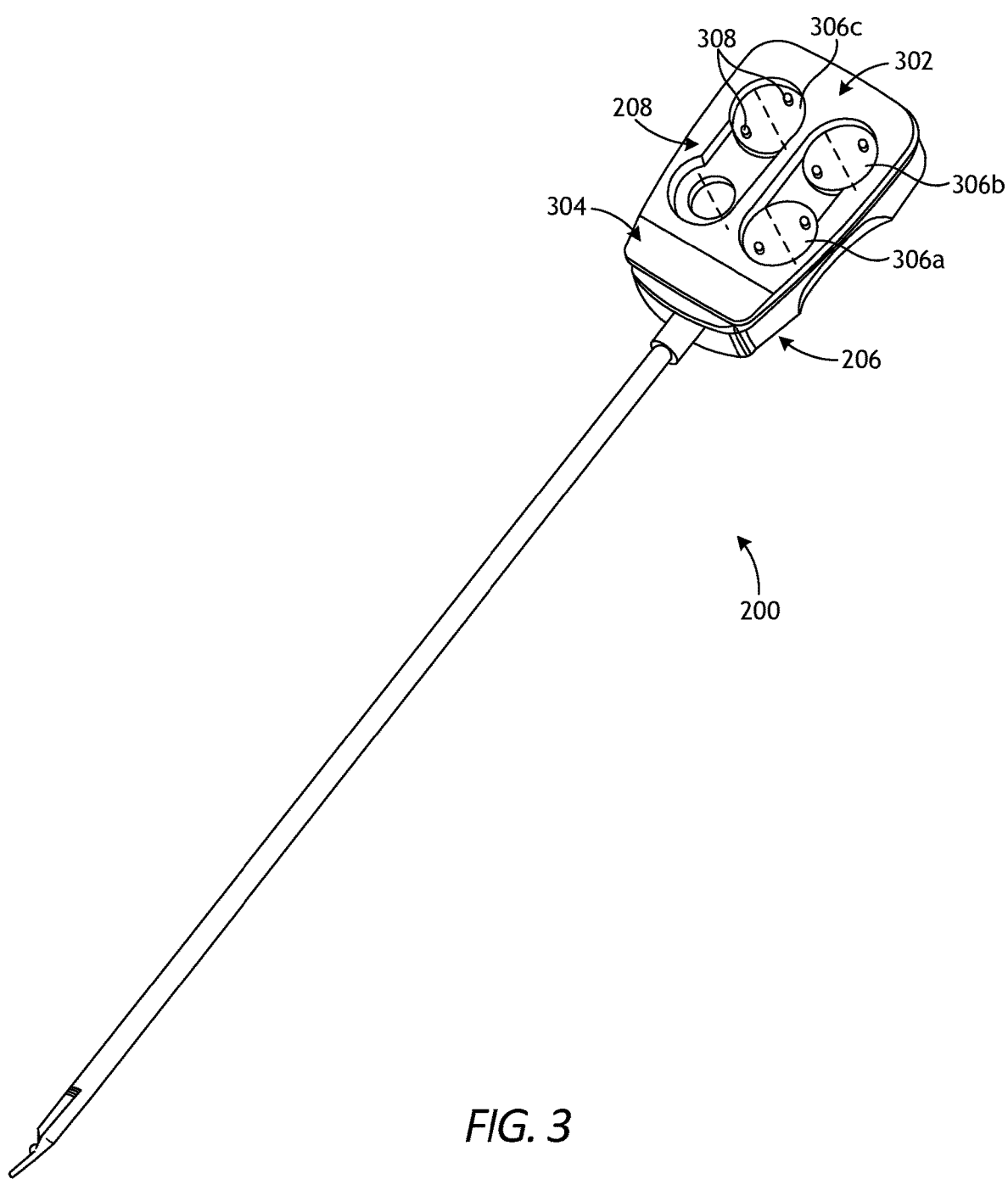
FIG. 3 is an isometric bottom view of the surgical tool of FIG. 2.

FIG. 3 is an isometric bottom view of the surgical tool 200. The surgical tool 200 further includes an interface 302 that mechanically and electrically couples the tool mounting portion 208 to a robotic manipulator. In various embodiments, the tool mounting portion 208 includes a tool mounting plate 304 that operably supports a plurality of drive inputs, shown as a first drive input 306a, a second drive input 306b, and a third drive input 306c. While only three drive inputs 306a-c are shown in FIG. 3, more or less than three may be employed, without departing from the scope of the disclosure.

In the illustrated embodiment, each drive input 306a-c comprises a rotatable disc configured to align with and couple to a corresponding input actuator (not shown) of a given tool driver. Moreover, each drive input 306a-c provides or defines one or more surface features 308 configured to align with mating surface features provided on the corresponding input actuator. The surface features 308 can include, for example, various protrusions and/or indentations that facilitate a mating engagement.

Figure 4:
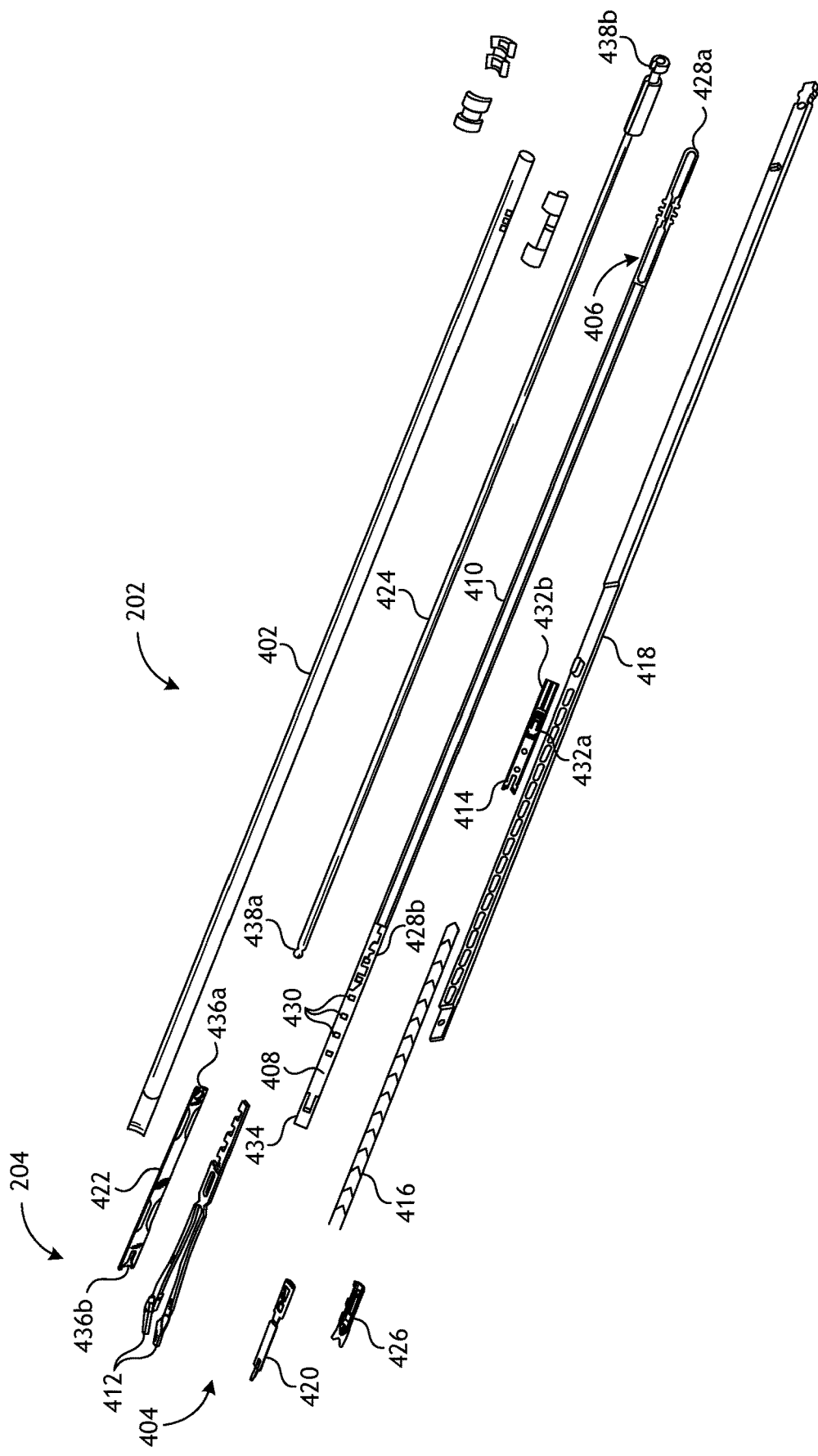
FIG. 4 is an exploded view of the elongate shaft and the end effector of the surgical tool of FIGS. 2 and 3.

FIG. 4 is an exploded view of one example of the elongate shaft 202 and the end effector 204 of the surgical tool 200 of FIGS. 2 and 3, according to one or more embodiments. As illustrated, the shaft 202 includes an outer tube 402 that houses the various components of the shaft 202, which can include a jaw retaining assembly 404. The jaw retaining assembly 404 includes a jaw retainer shaft 406 with a clip track 408 and a push rod channel 410 formed thereon. The end effector 204 includes opposing jaws 412 that are configured to mate to a distal end of the clip track 408.

The shaft 202 also includes a clip advancing assembly, which, in one example embodiment, can include a feeder shoe 414 adapted to be slidably disposed within the clip track 408. The feeder shoe 414 is designed to advance a series of clips 416 positioned within the clip track 408, and a feedbar 418 is adapted to drive the feeder shoe 414 through the clip track 408. An advancer assembly 420 is adapted to mate to a distal end of the feedbar 418 for advancing a distal-most clip into the jaws 412.

The shaft 202 furthers include a clip forming or camming assembly operable to collapse the jaws 412 and thereby crimp (crush) a surgical clip 416 positioned between (interposing) the jaws 412. The camming assembly includes a cam 422 that slidably mates to the jaws 412, and a push rod 424 that moves the cam 422 relative to the jaws 412 to collapse the jaws 412. A tissue stop 426 can mate to a distal end of the clip track 408 to help position the jaws 412 relative to a surgical site.

The jaw retainer shaft 406 is extendable within and couples to the outer tube 402 at a proximal end 428a, and its distal end 428b is adapted to mate with the jaws 412. The push rod channel 410 formed on the jaw retainer shaft 406 may be configured to slidably receive the push rod 424, which is used to advance the cam 422 over the jaws 412. The clip track 408 extends distally beyond the distal end 428b of the jaw retainer shaft 406 to allow a distal end of the clip track 408 to be substantially aligned with the jaws 412.

The clip track 408 can include several openings 430 formed therein for receiving an upper or "superior" tang 432a formed on the feeder shoe 414 adapted to be disposed within the clip track 408. The clip track 408 can also include a stop tang 434 formed thereon that is effective to be engaged by a corresponding stop tang formed on the feeder shoe 414 to prevent movement of the feeder shoe 414 beyond a distal-most position. To facilitate proximal-movement of the feeder shoe 414 within the clip track 408, the feeder shoe 414 can also include a lower or "inferior" tang 432b formed on the underside thereof for allowing the feeder shoe 414 to be engaged by the feedbar 418 as the feedbar 418 is moved distally. In use, each time the feedbar 418 is moved distally, a detent formed in the feedbar 418 engages the inferior tang 432b and moves the feeder shoe 414 distally a predetermined distance within the clip track 408. The feedbar 418 can then be moved proximally to return to its initial position, and the angle of the inferior tang 432b allows the inferior tang 432b to slide into the next detent formed in the feedbar 418.

The jaws 412 include first and second opposed jaw members that are movable (collapsible) relative to one another and are configured to receive a surgical clip from the series of clips 416 therebetween. The jaw members can each include a groove formed on opposed inner surfaces thereof for receiving the legs of a surgical clip 416 in alignment with the jaw members. In the illustrated embodiment, the jaw members are biased to an open position and a force is required to urge the jaw members toward one another to crimp the interposing clip 416. The jaw members can also each include a cam track formed thereon for allowing the cam 422 to slidably engage and move the jaw members toward one another. A proximal end 436a of the cam 422 is matable with a distal end 438a of the push rod 424, and a distal end 436b of the cam 422 is adapted to engage and actuate the jaws 412. The proximal end 438b of the push rod 424 is matable with a closure link assembly associated with the drive housing 206 for moving the push rod 424 and the cam 422 relative to the jaws 412.

The distal end 436b of the cam 422 includes a camming channel or tapering recess formed therein for slidably receiving corresponding cam tracks provided by the jaw members. In operation, the cam 422 is advanced from a proximal position, in which the jaw members are spaced apart from one another, to a distal position, where the jaw members are collapsed to a closed position. As the cam 422 is advanced over the jaw members, the tapering recess at the distal end 436b serves to push the jaw members toward one another, thereby crimping a surgical clip 416 disposed therebetween.

Figure 5:
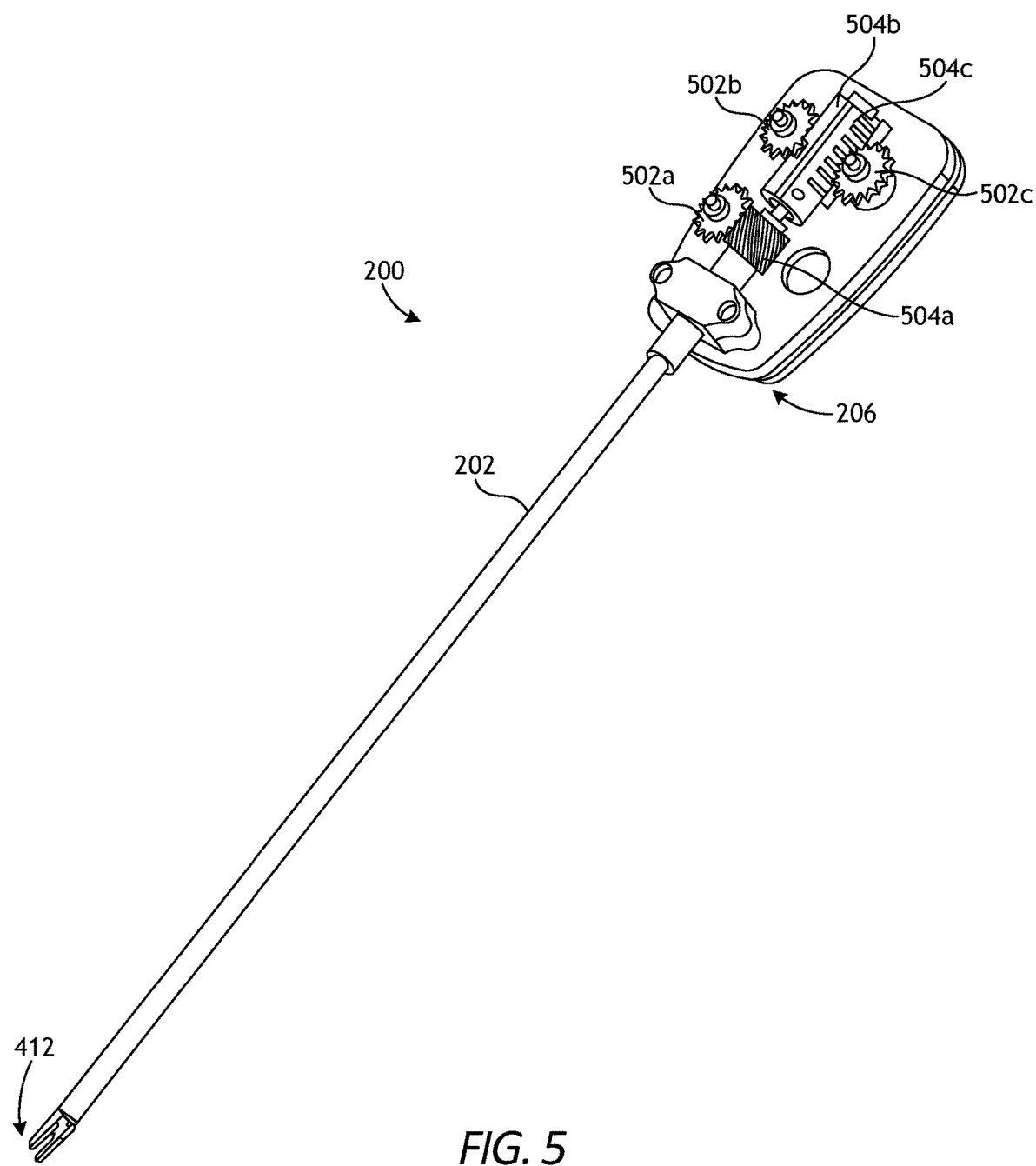
FIG. 5 is an exposed isometric view of the surgical tool of FIG. 2.

FIG. 5 is an exposed isometric view of the surgical tool 200 of FIG. 2, according to one or more embodiments. The shroud or covering of the drive housing 206 has been removed to reveal the internal component parts. As illustrated, the surgical tool 200 may include a first drive gear 502a, a second drive gear 502b, and a third drive gear 502c. The first drive gear 502a may be operatively coupled to (or extend from) the first drive input 306a (FIG. 3) such that actuation of the first drive input 306a correspondingly rotates the first drive gear 502a. Similarly, the second and third drive gears 502b,c may be operatively coupled to (or extend from) the second and third drive inputs 306b,c (FIG. 3), respectively, such that actuation of the second and third drive inputs 306b,c correspondingly rotates the second and third drive gears 502b,c, respectively.

The first drive gear 502a may be configured to intermesh with a first driven gear 504a, which is operatively coupled to the shaft 202. In the illustrated embodiment, the driven gear 504a comprises a helical gear. In operation, rotation of the first drive gear 502a about a first axis correspondingly rotates the first driven gear 504a about a second axis orthogonal to the first axis to control rotation of the shaft 202 in clockwise and counter-clockwise directions based on the rotational direction of the first drive gear 502a.

The second drive gear 502b may be configured to intermesh with a second driven gear 504b (partially visible in FIG. 5), and the third drive gear 502c may be configured to intermesh with a third driven gear 504c. In the illustrated embodiment, the second and third drive and driven gears 502b,c, 504b,c comprise corresponding rack and pinion interfaces, where the driven gears 504b,c comprise the rack and the drive gears 502b,c comprise the pinion. Independent rotation of the second and third drive gears 502b,c will cause the second and third driven gears 504b,c, respectively, to translate linearly relative to (independent of) one another.

In at least one embodiment, actuation (rotation) of the third drive gear 502c will result in a surgical clip 416 (FIG. 4) being fed into the jaws 412. More particularly, the third driven gear 504c may be operatively coupled to the feedbar 418 (FIG. 4) and, upon rotation of the third drive gear 502c in a first angular direction, the third driven gear 504c will advance distally and correspondingly advance the feedbar 418 a sufficient distance to fully advance a surgical clip into the jaws 412. Rotation of the third drive gear 502c may be precisely controlled by an electrical and software interface to deliver the exact linear travel to the third driven gear 504c necessary to feed a clip 416 into the jaws 412.

Upon delivery of a clip into the jaws 412, or after a predetermined amount of rotation of the third drive gear 502c, rotation of the third drive gear 502c is reversed in a second angular direction to move the third driven gear 504c linearly in a proximal direction, which correspondingly moves the feedbar 418 proximally. This process may be repeated several times to accommodate a predetermined number of clips residing in the shaft 202.

Actuation of the second drive gear 502b causes the jaws 412 to close or collapse to crimp a surgical clip. More particularly, the second driven gear 504b may be coupled to the proximal end 438b (FIG. 4) of the push rod 424 (FIG. 4) and, upon actuation of the second drive gear 502b in a first angular direction, the second driven gear 504b will be advanced linearly in a distal direction and correspondingly drive the push rod 424 distally, which drives the cam 422 over the jaws 412 to collapse the jaw members and crimp a surgical clip positioned in the jaws 412. Once a surgical clip is successfully deployed, rotation of the second drive gear 502b is reversed in the opposite angular direction to move the second driven gear 504b in a proximal direction, which correspondingly moves the push rod 424 and the cam 422 proximally and permits the jaws 412 to open once again.

The processes of delivering a surgical clip into the jaws 412 and collapsing the jaws 412 to crimp the surgical clip are not limited to the actuation mechanisms and structures described herein. In alternative embodiments, for example, the second and third driven gears 504b,c may instead comprise capstan pulleys configured to route and translate drive cables within the shaft 202. In such embodiments, the drive cables may be operatively coupled to one or more lead screws or other types of rotating members positioned within the shaft 202 near the distal end and capable of advancing the feedbar 418 to deliver a surgical clip into the jaws 412 and advancing the cam 422 to collapse the jaws 412 and crimp the surgical clip.

Figure 6:
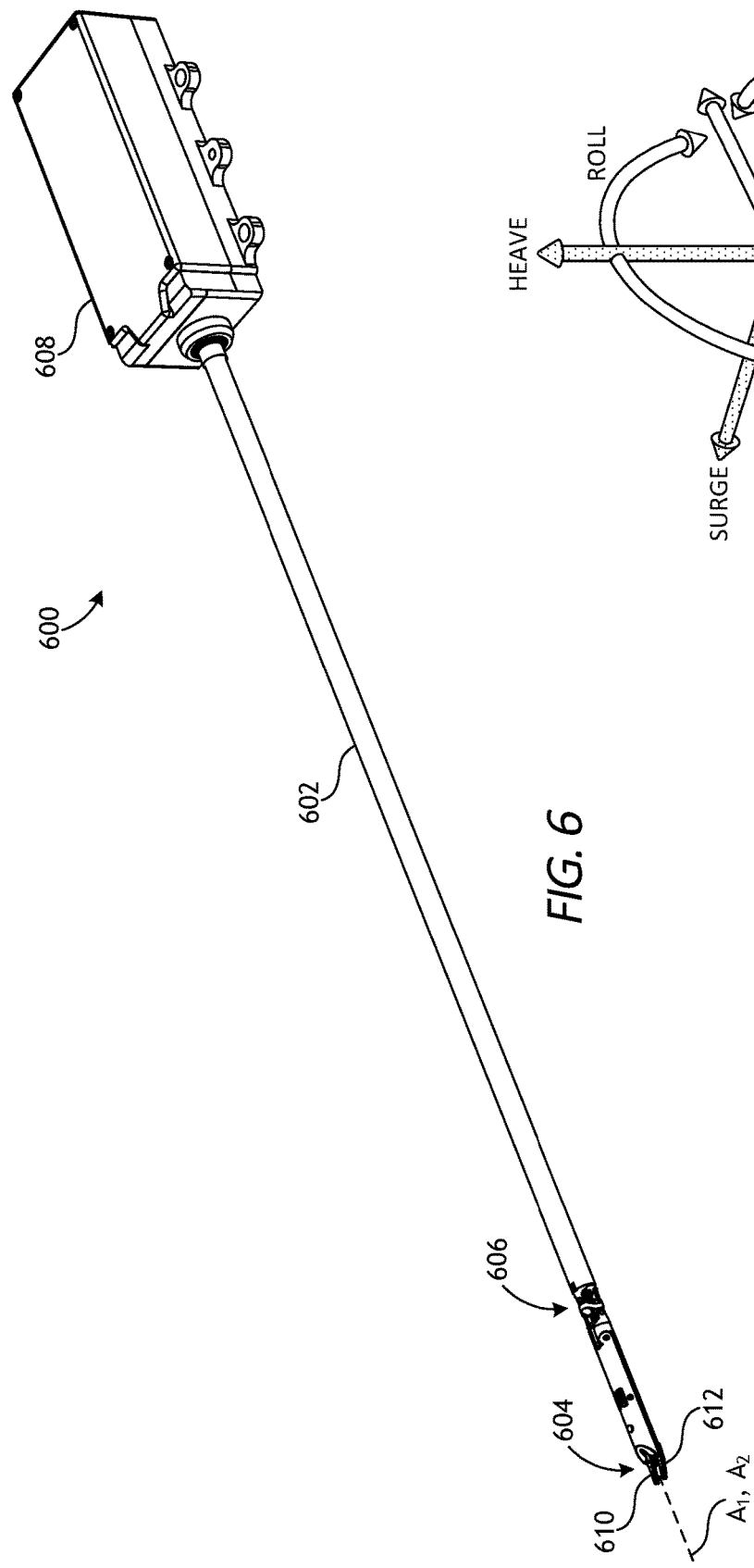
FIG. 6 is a side view of an example surgical tool that may incorporate some or all of the principles of the present disclosure.

FIG. 6 is an isometric top view of another example surgical tool 600 that may incorporate some or all of the principles of the present disclosure. Similar to the surgical tool 200 of FIG. 2, the surgical tool 600 may be used in conjunction with the robotic surgical system 100 of FIG. 1. As illustrated, the surgical tool 600 includes an elongate shaft 602, an end effector 604 positioned at the distal end of the shaft 602, an articulating joint 606 (alternately referred to as a "articulable wrist joint") that couples the end effector 604 to the distal end of the shaft 602, and a drive housing 608 coupled to the proximal end of the shaft 602. In some embodiments, the shaft 602, and hence the end effector 604 coupled thereto, is configured to rotate about a longitudinal axis $A_1$.

In the illustrated embodiment, the end effector 604 comprises a clip applier that includes opposing jaw members 610, 612 configured to collapse toward one another to crimp a surgical clip. The articulating joint 606 facilitates pivoting movement of the end effector 604 relative to the shaft 602 to position the end effector 604 at desired orientations and locations relative to a surgical site. The housing 608 includes (contains) various actuation mechanisms designed to control articulation at the articulating joint 606 and operation of the end effector 604.

Figure 7:
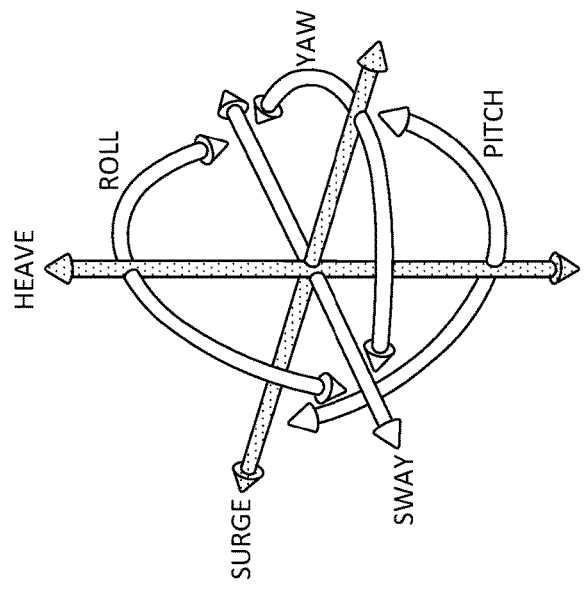
FIG. 7 illustrates potential degrees of freedom in which the wrist of FIG. 1 may be able to articulate (pivot).

FIG. 7 illustrates the potential degrees of freedom in which the articulating joint 606 may be able to articulate (pivot). The degrees of freedom of the articulating joint 606 are represented by three translational variables (i.e., surge, heave, and sway), and by three rotational variables (i.e., Euler angles or roll, pitch, and yaw). The translational and rotational variables describe the position and orientation of a component of a surgical system (e.g., the end effector 604) with respect to a given reference Cartesian frame. As depicted in FIG. 7, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the articulating joint 606 (e.g., X-axis), yaw movement about a second axis of the articulating joint 606 (e.g., Y-axis), and combinations thereof to allow for 360° rotational movement of the end effector 604 about the articulating joint 606. In other applications, the pivoting motion can be limited to movement in a single plane, e.g., only pitch movement about the first axis of the articulating joint 606 or only yaw movement about the second axis of the articulating joint 606, such that the end effector 604 moves only in a single plane.

Referring again to FIG. 6, the surgical tool 600 includes a plurality of drive cables (generally obscured in FIG. 6) that form part of a cable driven motion system configured to facilitate operation and articulation (movement) of the end effector 604 relative to the shaft 602. For example, selectively moving the drive cables can actuate the end effector 604 and thereby collapse the jaw members 610, 612 toward each other. Moreover, moving the drive cables can also move the end effector 604 between an unarticulated position and an articulated position. The end effector 604 is depicted in FIG. 6 in the unarticulated position where a longitudinal axis $A_2$ of the end effector 604 is substantially aligned with the longitudinal axis $A_1$ of the shaft 602, such that the end effector 604 is at a substantially zero angle relative to the shaft 602. In the articulated position, the longitudinal axes $A_1$, $A_2$ would be angularly offset from each other such that the end effector 604 is at a non-zero angle relative to the shaft 602.

Figure 8:
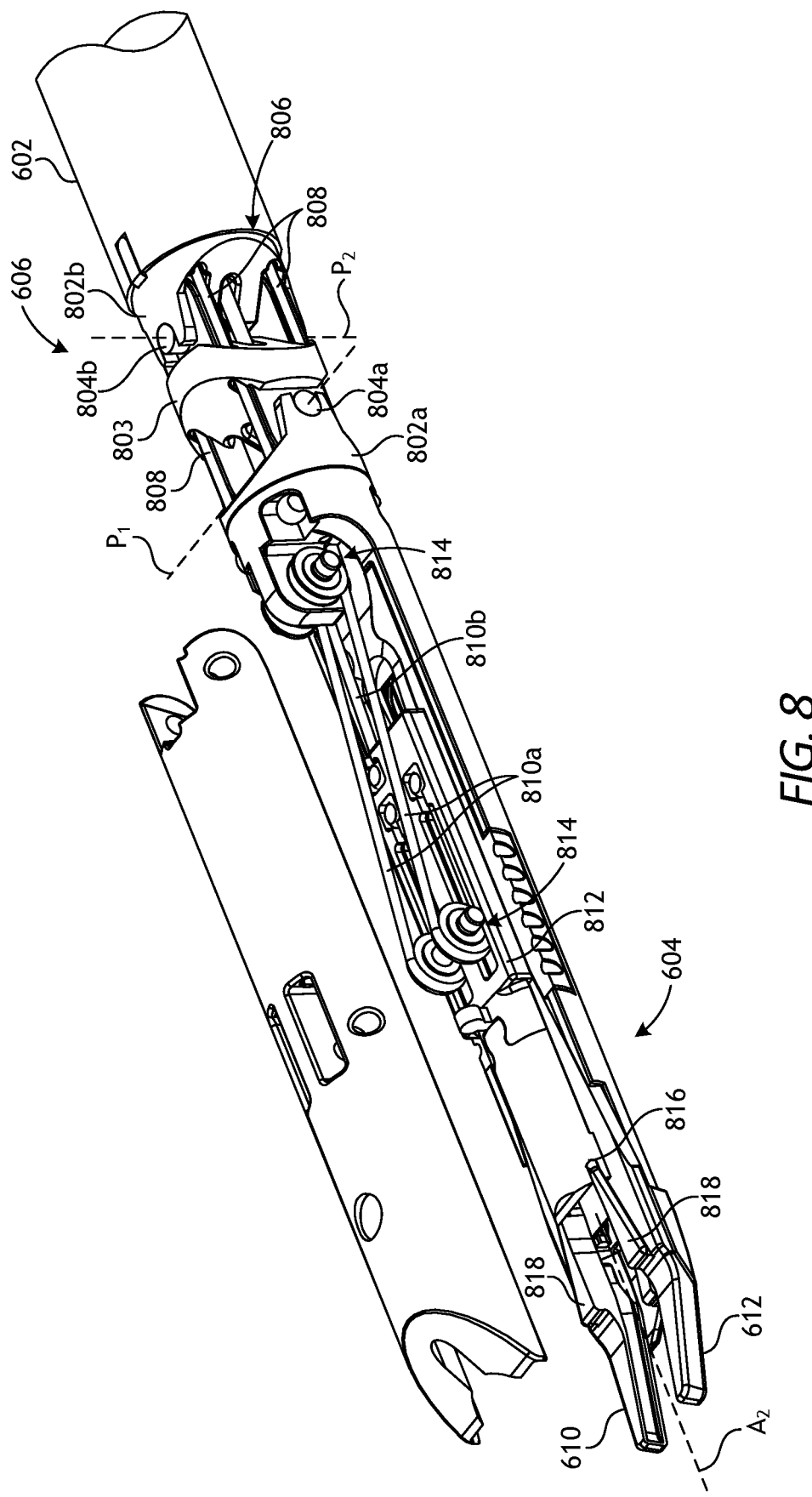
FIG. 8 is an enlarged isometric view of the distal end of the surgical tool of FIG. 6.

FIG. 8 is an enlarged isometric view of the distal end of the surgical tool 600 of FIG. 6. More specifically, FIG. 8 depicts an enlarged and partially exploded view of the end effector 604 and the articulating joint 606. The articulating joint 606 operatively couples the end effector 604 to the shaft 602. To accomplish this, the articulating joint 606 includes a distal clevis 802a, a proximal clevis 802b, and a spacer 803 interposing the distal and proximal clevises 802a,b. The end effector 604 is coupled to the distal clevis 802a and the distal clevis 802a is rotatably mounted to the spacer 803 at a first axle 804a. The spacer 803 is rotatably mounted to the proximal clevis 802b at a second axle 804b and the proximal clevis 802b is coupled to a distal end 806 of the shaft 602.

The articulating joint 606 provides a first pivot axis $P_1$ that extends through the first axle 804a and a second pivot axis $P_2$ that extends through the second axle 804b. The first pivot axis $P_1$ is substantially perpendicular (orthogonal) to the longitudinal axis $A_2$ of the end effector 604, and the second pivot axis $P_2$ is substantially perpendicular (orthogonal) to both the longitudinal axis $A_2$ and the first pivot axis $P_1$. Movement about the first pivot axis $P_1$ provides "yaw" articulation of the end effector 604, and movement about the second pivot axis $P_2$ provides "pitch" articulation of the end effector 604.

A plurality of drive cables 808 extend longitudinally within the shaft 602 and pass through the wrist 106 to be operatively coupled to the end effector 604. The drive cables 808 form part of the cable driven motion system briefly described above, and may be referred to and otherwise characterized as cables, bands, lines, cords, wires, ropes, strings, twisted strings, elongate members, etc. The drive cables 808 can be made from a variety of materials including, but not limited to, metal (e.g., tungsten, stainless steel, etc.) or a polymer.

The drive cables 808 extend proximally from the end effector 604 to the drive housing 608 (FIG. 6) where they are operatively coupled to various actuation mechanisms or devices housed (contained) therein to facilitate longitudinal movement (translation) of the drive cables 808. Selective actuation of the drive cables 808 causes the end effector 604 to articulate (pivot) relative to the shaft 602. Moving a given drive cable 808 constitutes applying tension (i.e., pull force) to the given drive cable 808 in a proximal direction, which causes the given drive cable 808 to translate and thereby cause the end effector 604 to move (articulate) relative to the shaft 602.

One or more actuation cables 810, shown as first actuation cables 810a and second actuation cables 810b, may also extend longitudinally within the shaft 602 and pass through the wrist 106 to be operatively coupled to the end effector 604. The actuation cables 810a,b may be similar to the drive cables 808 and also form part of the cable driven motion system. Selectively actuating the actuation cables 810a,b causes the end effector 604 to actuate, such as collapsing the first and second jaw members 610, 612 to crimp a surgical clip (not shown).

More specifically, the actuation cables 810a,b may be operatively coupled to a cam 812 that is slidably engageable with the jaw members 610, 612. One or more pulleys 814 may be used to receive and redirect the first actuation cables 810a for engagement with the cam 812. Longitudinal movement of the first actuation cables 810a correspondingly moves the cam 812 distally relative to the jaw members 610, 612. The distal end of the cam 812 includes a tapering recess or camming channel 816 formed therein for slidably receiving corresponding cam tracks 818 provided by the jaw members 610, 612. As the cam 812 is advanced distally, the camming channel 816 pushes (collapses) the jaw members 610, 612 toward one another, thereby crimping a surgical clip (not shown) disposed therebetween. Actuation of the second actuation cables 810b (one shown) pulls the cam 812 proximally, thereby allowing the jaw members 610, 612 to open again to receive another surgical clip.

Although not expressly depicted in FIG. 8, an assembly including, for example, a feedbar, a feeder shoe, and a clip track may be included at or near the end effector 604 to facilitate feeding surgical clips into the jaw members 610, 612. In some embodiments, the feedbar (or a connecting member) may be flexible and extend through the articulating joint 606.

Figure 9:
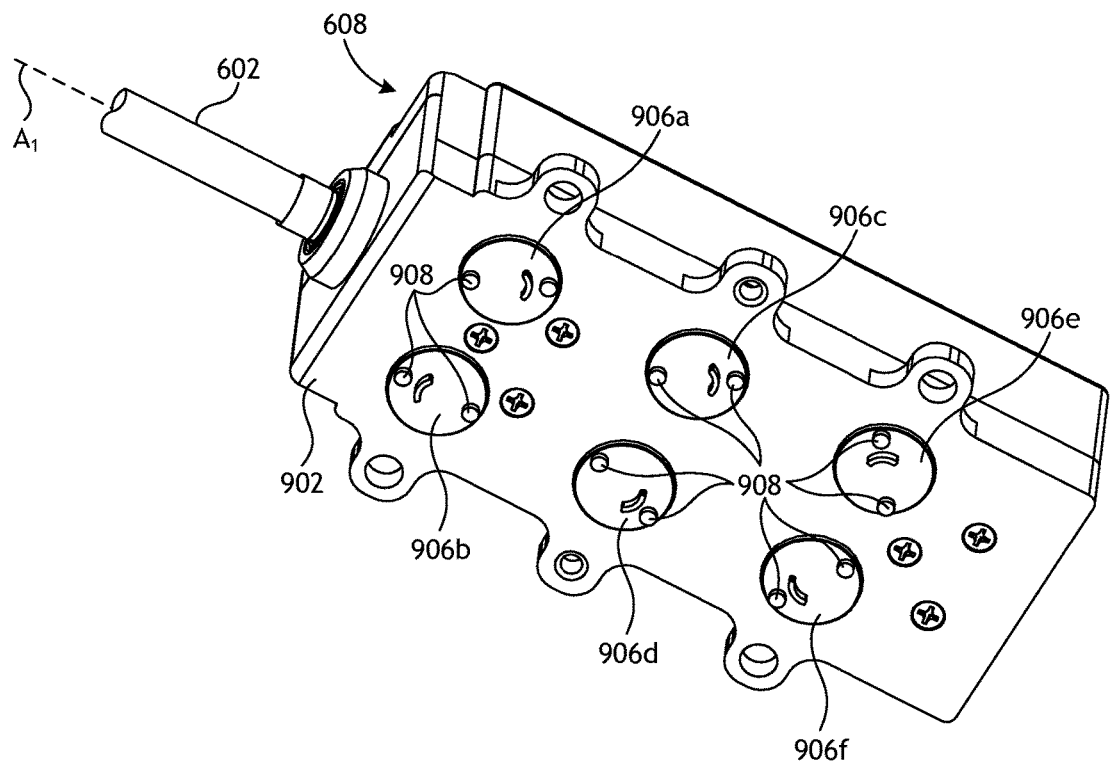
FIG. 9 is a bottom view of the drive housing of the surgical tool of FIG. 6.

FIG. 9 is a bottom view of the drive housing 608, according to one or more embodiments. As illustrated, the drive housing 608 may include a tool mounting interface 902 used to operatively couple the drive housing 608 to a tool driver of a robotic manipulator. The tool mounting interface 902 may mechanically, magnetically, and/or electrically couple the drive housing 608 to a tool driver.

As illustrated, the interface 902 includes and supports a plurality of drive inputs, shown as drive inputs 906a, 906b, 906c, 906d, 906e, and 906f. Each drive input 906a-f may comprise a rotatable disc configured to align with and couple to a corresponding input actuator (not shown) of a tool driver. Moreover, each drive input 906a-f provides or defines one or more surface features 908 configured to align with mating features provided on the corresponding input actuator. The surface features 908 can include, for example, various protrusions and/or indentations that facilitate a mating engagement.

In some embodiments, actuation of the first drive input 906a may control rotation of the elongate shaft 602 about its longitudinal axis $A_1$. Depending on the rotational actuation of the first drive input 906a, the elongate shaft 602 may be rotated clockwise or counter-clockwise. In some embodiments, selective actuation of the second and third drive inputs 906b,c may cause movement (axial translation) of the actuation cables 810a,b (FIG. 8), which causes the cam 812 (FIG. 8) to move and crimp a surgical clip, as generally described above. In some embodiments, actuation of the fourth drive input 906d feeds a surgical clip into the jaw members 610, 612 (FIG. 8). In some embodiments, actuation of the fifth and sixth drive inputs 906e,f causes movement (axial translation) of the drive cables 808 (FIG. 8), which results in articulation of the end effector 604. Each of the drive inputs 906a-f may be actuated based on user inputs communicated to a tool driver coupled to the interface 902, and the user inputs may be received via a computer system incorporated into the robotic surgical system.

Figure 10:
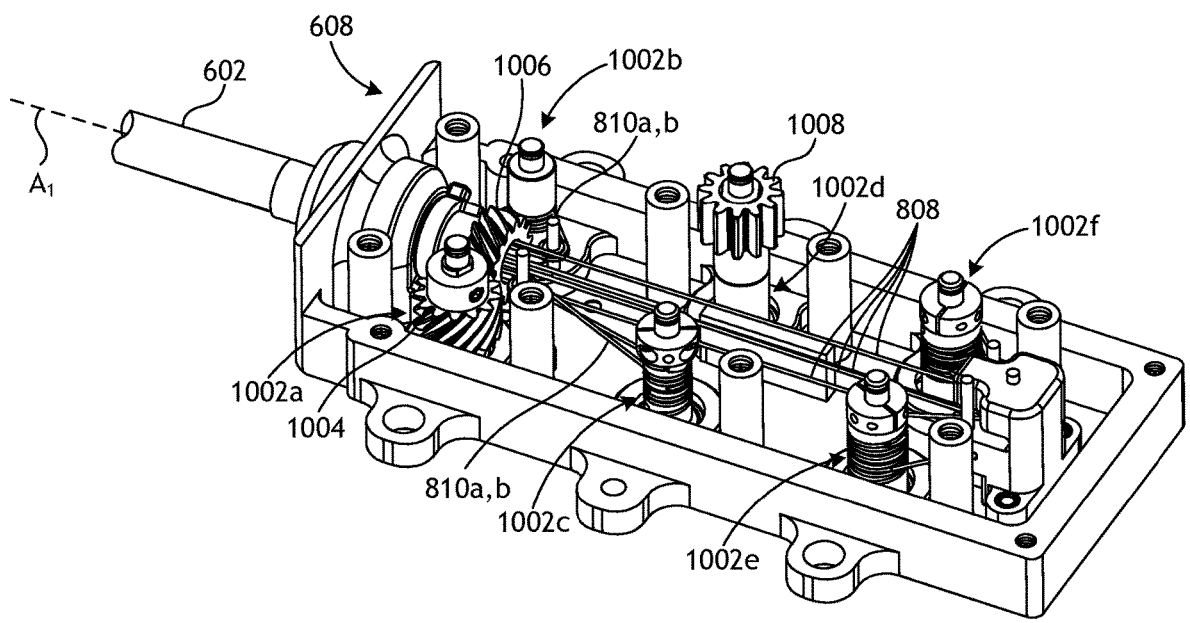
FIG. 10 is an isometric exposed view of the interior of the drive housing of the surgical tool of FIG. 6.

FIG. 10 is an isometric exposed view of the interior of the drive housing 608, according to one or more embodiments. Several component parts that may otherwise be contained within the drive housing 608 are not shown in FIG. 10 to enable discussion of the depicted component parts.

As illustrated, the drive housing 608 contains a first capstan 1002a, which is operatively coupled to or extends from the first drive input 906a (FIG. 9) such that actuation of the first drive input 906a results in rotation of the first capstan 1002a. A helical drive gear 1004 is coupled to or forms part of the first capstan 1002a and is configured to mesh and interact with a driven gear 1006 operatively coupled to the shaft 602 such that rotation of the driven gear 1006 correspondingly rotates the shaft 602. Accordingly, rotation of the helical drive gear 1004 (via actuation of the first drive input 906a of FIG. 9) will drive the driven gear 1006 and thereby control rotation of the elongate shaft 602 about the longitudinal axis $A_1$.

The drive housing 608 also includes second and third capstans 1002b and 1002c operatively coupled to or extending from the second and third drive inputs 906b,c (FIG. 9), respectively, such that actuation of the second and third drive inputs 906b,c results in rotation of the second and third capstans 1002b,c. The second and third capstans 1002b,c comprise capstan pulleys operatively coupled to the actuation cables 810a,b (FIG. 8) such that rotation of a given capstan 1002b,c actuates (longitudinally moves) a corresponding one of the actuation cables 810a,b. Accordingly, selective rotation of the second and third capstans 1002b,c via actuation of the second and third drive inputs 906b,c, respectively, will cause movement (axial translation) of the actuation cables 810a,b, which causes the cam 812 (FIG. 8) to move and crimp a surgical clip.

The drive housing 608 further includes a fourth capstan 1002d, which is operatively coupled to or extends from the fourth drive input 906d (FIG. 9) such that actuation of the fourth drive input 906d results in rotation of the fourth capstan 1002d. A spur gear 1008 is coupled to or forms part of the fourth capstan 1002d and is configured to mesh and interact with a rack gear (not shown) also contained within the drive housing 608. The rack gear may be operatively coupled to a feedbar (or another connecting member) which facilitates operation of a feeder shoe and associated clip track to feed surgical clips into the jaw members 610, 612 (FIGS. 6 and 8). Accordingly, rotation of the spur gear 1008 (via actuation of the fourth drive input 906d) will control the feedbar and thereby control loading of surgical clips into the jaw members 610, 612 as desired.

The drive housing 608 further contains or houses fifth and sixth capstans 1002e and 1002f operatively coupled to or extending from the fifth and sixth drive inputs 906e,f (FIG. 9), respectively, such that actuation of the fifth and sixth drive inputs 906e,f results in rotation of the fifth and sixth capstans 1002e,f. The fifth and sixth capstans 1002e,f comprise capstan pulleys operatively coupled to the drive cables 808 (FIG. 8) such that rotation of a given capstan 1002e,f actuates (longitudinally moves) a corresponding one of the actuation cables 808. Accordingly, selective rotation of the fifth and sixth capstans 1002e,f via actuation of the fifth and sixth drive inputs 906e,f, respectively, will cause movement (axial translation) of the drive cables 808 and thereby articulate (pivot) the end effector 604 relative to the shaft 602.

The surgical tools 200, 600 described herein above may incorporate and facilitate the principles of the present disclosure in improving feeding and/or forming of surgical clips in robotic or non-robotic clip appliers. Moreover, it is contemplated herein to combine some or all of the features of the surgical tools 200, 600 to facilitate operation of the embodiments described below. Accordingly, example surgical tools that may incorporate the principles of the present disclosure may include geared actuators, capstan pulley and cable actuators, or any combination thereof, without departing from the scope of the disclosure.

Figure 11:
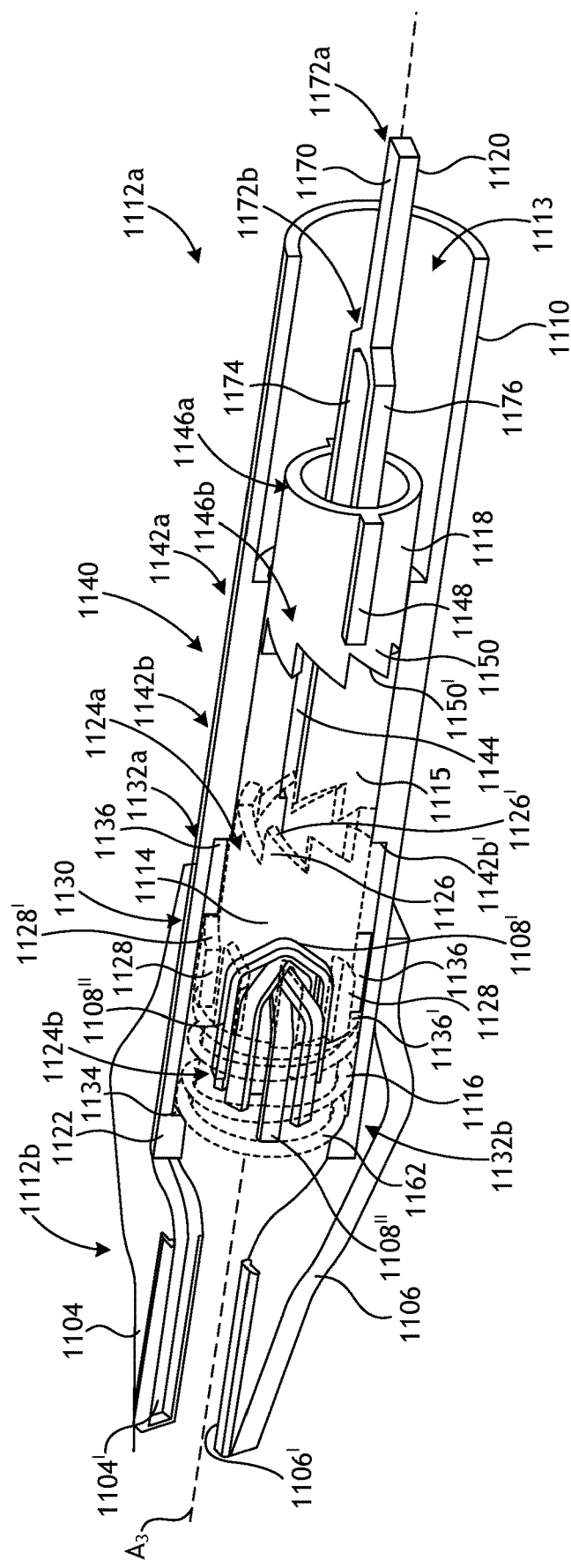
FIG. 11 is an exposed, partial cross-sectional side view of an example end effector.

FIG. 11 is an enlarged isometric cross-sectional view of an example end effector 1102, according to one or more embodiments of the present disclosure. The end effector 1102 may be similar in some respects to the end effectors 204 and 604 of FIGS. 2 and 6, respectively. Similar to the end effectors 204, 604, for example, the end effector 1102 may be incorporated into either or both of the surgical tools 200, 600 described herein above. In addition, the end effector 1102 may comprise a clip applier having opposed jaw members 1104 and 1106 configured to collapse toward one another to crimp a surgical clip 1108 (four shown in a stacked arrangement). As described herein, the end effector 1102 may incorporate various component parts and actuatable mechanisms or features that facilitate the feeding of the surgical clip(s) 1108 into the opposed jaw members 1104,1106 and collapsing the opposed jaw members 1104, 1106 to crimp the surgical clip(s) 1108 when desired. Moreover, the corresponding inner surfaces of each of the opposed jaw members 1104,1106 may define or otherwise provide a groove 1104',1106' that together define a path, slot, or track that the surgical clips 1108 may travel as they are pushed or fed into interposition between the opposed jaw members 1104,1106, as hereinafter described.

As illustrated, the end effector 1102 extends along a longitudinal axis $A_3$ and includes an elongate body 1110 having a proximal end 1112a and a distal end 1112b. The jaw members 1104,1106 extend out of or otherwise past the distal end 1112b. In addition, the end effector 1102 includes a revolver 1114, a biasing member 1116, an indexer 1118, and a clip advancer 1120 (referred to hereinafter as an "advancer") that are each arranged within the body 1110. The indexer 1118 and the pusher 1120 may be longitudinally actuatable (movable) to cause the revolver 1114 to index (rotate) and thereby selectively discharge a surgical clip 1108 housed within the revolver 1114. To accomplish this, the indexer 1118 and the pusher 1120 may be operatively coupled to a drive input of a drive housing, such as one of the drive housings 206, 608 of FIGS. 2 and 6, respectively. In such embodiments, for example, the indexer 1118 and the pusher 1120 may be operatively coupled to the second and third drive and driven gears 502b,c, 504b,c of FIG. 5 or one or more of the rotatable capstans 1002b-f of FIG. 10.

The surgical clips 1108 may be housed within the revolver 1114, and the indexer 1118 may be actuatable to longitudinally translate to engage and index the revolver 1114. Indexing the revolver 1114 selectively facilitates sequential axial alignment of each surgical clip 1108 with the opposed jaw members 1104,1106, as hereinafter described. Thereafter, the pusher 1120 may be actuatable to discharge and deploy the aligned surgical clip 1108 from the revolver 1114 and into interposition between the opposed jaw members 1104,1106 where it can be crimped.

As illustrated, the body 1110 is generally cylindrical and hollow. Consequently, the body 1110 defines a bore 1113 that extends the length of the end effector 1102, from the proximal end 1112a to the distal end 1112b. As described below, the bore 1113 may comprise various regions or compartments that house or otherwise accommodate the revolver 1114, the indexer 1118, and the pusher 1120. The body 1110 defines an annular flange 1122 at the distal end 1112b and an interior surface 1115 of the bore 1113 extends proximally therefrom. In some embodiments, the proximal end 1112a may be operatively coupled to an elongate shaft of a surgical tool, such as the shaft 202 of the surgical tool 200 of FIG. 2. In other embodiments, however, the proximal end 1112a may be operatively coupled to an articulable wrist joint, such as the wrist 606 of the surgical tool 600 of FIG. 6.

The revolver 1114 includes a proximal end 1124a and a distal end 1124b. The revolver 1114 may be hollow to accommodate the surgical clips 1108 at or near the distal end 1124b. Each surgical clip 1108 includes a crown 1108' (alternately referred to as an "apex") and a pair of legs 1108" extending longitudinally from the crown 1108'. As illustrated, the surgical clips 1108 are stored within the clip revolver 1114 in a nested helical array. As used herein in conjunction with the stacking arrangement of the surgical clips 1108, the phrase "nested helical array" refers to the surgical clips 1108 being arranged (stacked) with the crown of the more proximal surgical clips 1108 stacked upon (or in close proximity to) the crown of the more distal surgical clips, and the legs of the more proximal surgical clips 1108 extending past the crown of the more distal surgical clips 1108, and where the legs of all the surgical clips 1108 extend substantially parallel to the longitudinal axis $A_3$. Moreover, "nested helical array" also refers to the surgical clips 1108 being stacked such that they are angularly offset from each other. More specifically, the surgical clips 1108 are stacked such that each successive surgical clip 1108 resides in a different radial plane relative to the longitudinal axis $A_3$. Accordingly, the surgical clips 1108 are arranged within the clip revolver 1114 with the legs 1108" leading towards the jaw members 1104,1106 and the crown 1108' extending proximally therefrom. As a result, the surgical clips 1108 are fed legs 1108" first into the jaw members 1104,1106.

The revolver 1114 provides a plurality of cams 1126 defined at the proximal end 1124a. Each cam 1126 defines a corresponding camming surface 1126' engageable with the indexer 1118 to effect rotation of the revolver 1114, as described below. The revolver 1114 also provides or otherwise defines a plurality of guides 1128 arranged on an outer radial surface thereof. The guides 1128 are outwardly protruding features that are positioned between the proximal and distal ends 1124a,1124b, distal of the cams 1126, and may be equidistantly spaced about the outer radial surface of the revolver 1114. Each guide 1128 may define a camming surface 1128' and, in some embodiments, each guide 1128 may axially align with a corresponding one of the cams 1126 such that the camming surfaces 1126',1128' have corresponding orientations. The revolver 1114 is further described below with reference to FIG. 12.

As mentioned above, the bore 1113 of the body 1110 includes one or more discrete internal regions or compartments that are formed into the body 1110. In the illustrated embodiment, the bore 1113 defines or provides a revolver compartment 1130 and an indexer compartment 1140 that each extend along the longitudinal axis $A_3$. Here, the revolver compartment 1130 is proximate to the distal end 1112b and exhibits an increased diameter section of the bore 1113 that extends proximally from the annular flange 1122. The indexer compartment 1140 is located proximal to the revolver compartment 1130. The revolver 1114 and the indexer 1118 are disposed within the body 1110 and are each arranged to slide or translate along the longitudinal axis $A_3$ at least partially into the revolver compartment 1130 and the indexer compartment 1140. The revolver 1114 is also arranged to rotate about the longitudinal axis $A_3$. Rotating the revolver 1114 may be configured to sequentially align each surgical clip 1108 with the opposed jaw members 1104,1106.

The revolver compartment 1130 includes a proximal region 1132a and a distal region 1132b, where the distal region 1132b extends proximally from an interior lip 1134 of the annular flange 1122 and terminates at the indexer compartment 1140. The indexer compartment 1140 includes a proximal region 1142a and a distal region 1142b, where the distal region 1142b extends proximally from the revolver compartment 1130. In the illustrated embodiment, the indexer compartment 1140 has a smaller diameter than the revolver compartment 1130, thereby defining a distally facing annular face 1142b' that marks the intersection of the revolver compartment 1130 and the indexer compartment 1140.

The revolver compartment 1130 includes a plurality of camming grooves 1136 defined in the body 1110 and sized to slidably receive the guides 1128. In the illustrated embodiment, the camming grooves 1136 are axially aligned with and otherwise extend parallel to the longitudinal axis $A_3$, but they may alternatively have different orientations in other embodiments. Similar to the guides 1128, the camming grooves 1136 may be equidistantly spaced about the inner surface of the body 1110. Moreover, the number of guides 1128 and camming grooves 1136 may be generally the same, but could be different in alternative embodiments.

The revolver 1114 and the indexer 1118 may translate relative to the revolver compartment 1130 and the indexer compartment 1140 without being caught, impeded, or obstructed by the distally facing annular face 1142b' or any other protruding corners or edges formed at the intersection of the camming grooves 1136 and the indexer compartment 1140. Each camming groove 1136 may also define a camming surface 1136' at a distal end thereof that is engageable with a corresponding one of the camming surfaces 1128' of the guides 1128. Accordingly, the camming surfaces 1136' of the camming grooves 1136 and the camming surfaces 1128' may be substantially alignable when the revolver 1114 rotates (indexes) and may exhibit corresponding and complementary geometries. In addition, the camming surfaces 1136',1128' may also be cooperatively angled or oriented to help properly orient the guides 1128 within the camming grooves 1136.

Each camming groove 1136 may be configured to receive a corresponding one of the guides 1128 and thereby direct the revolver 1114 along a path defined by the geometry of the corresponding camming grooves 1136. More specifically, the camming grooves 1136 extend longitudinally and guide the revolver 1114 along a linear path when the guides 1128 are fully received therein. Thus, as the revolver 1114 translates proximally into the proximal region 1132a of the revolver compartment 1130, the guides 1128 are received within the camming grooves 1136 so that the revolver 1114 travels linearly without rotation. As the revolver 1114 travels distally during operation, the guides 1128 will eventually exit the camming grooves 1136 to allow the revolver 1114 to rotate (index).

The indexer compartment 1140 is configured to receive the indexer 1118, at least when the end effector 1102 is unactuated, such that the indexer 1118 may slide therein. In addition, the indexer compartment 1140 may partially receive the revolver 1114 during operation. Here, the cams 1126 of the revolver 1114 may extend into the distal region 1142b of the indexer compartment 1140, for example, when the end effector 1102 is unactuated.

The indexer 1118 may be configured to travel (reciprocate) within the indexer compartment 1140. To help guide and orient the indexer 1118 as it translates within the indexer compartment 1140, the body 1110 may define one or more indexer guides 1144 (one shown). In the illustrated embodiment, the indexer guides 1144 are channels, recesses, or tracks that are formed into the inner surface of the indexer compartment 1140 and extend longitudinally. The indexer guides 1144 may be configured to slidably receive one or more corresponding indexer rails 1148 (two shown) provided on the outer radial surface of the indexer 1118 and thereby orient the indexer 1118 as it travels between the proximal region 1142a and the distal region 1142b.

While the illustrated embodiment includes a pair of indexer rails 1148, it will be appreciated that more or less may be utilized, depending on the number of indexer guides 1144. Also, while the indexer rails 1148 are illustrated as being oriented with the longitudinal axis $A_3$ and extending from a proximal end 1146a to a distal end 1146b of the indexer 1118, the indexer rails 1148 may alternatively exhibit different geometries. For example, one or both of the indexer rails 1148 may be replaced with one or more pins or protrusions that are receivable within the indexer guides 1144. In even other embodiments, the indexer rails 1148 may be provided as recesses (grooves) configured to receive corresponding indexer guides 1144 in the form of protrusions.

The indexer guides 1144 may direct the indexer 1118 along various predetermined paths. Here, the indexer guides 1144 are linear (extend longitudinally) and thus inhibit rotation of the indexer 1118 about the longitudinal axis $A_3$. In other embodiments, however, the indexer guides 1144 may be non-linear and extend helically around the inner surface.

As mentioned, the indexer 1118 may be operatively coupled to a drive input of a drive housing (e.g., one of the drive housings 206, 608 of FIGS. 2 and 6, respectively). The proximal end 1146a of the indexer 1118 may be operatively connected to one or more members extending through the elongate shaft 202, 602 (FIGS. 2 and 6, respectively) such that it may be actuated. For example, the proximal end 1146a may be attached to a thrust shaft that extends through the length of the elongate shaft 202, 602 and may extend from one of the drive inputs included in the drive housing. However, the indexer 1118 may be differently reciprocated without departing from the present disclosure. Upon actuation, the indexer 1118 may be moved distally within the bore 1113 of the body 1110 and thereby engage and cause the revolver 1114 to index (rotate).

The indexer 1118 causes the revolver 1114 to index by engaging the cams 1126 of the revolver 1114. In the illustrated embodiment, the indexer 1118 includes a plurality of cams 1150 disposed on the distal end 1146b of the indexer 1118, and each cam 1150 defines a camming surface 1150' configured to engage a corresponding one of the camming surfaces 1126' of the revolver 1114. The camming surfaces 1126',1150' may have corresponding geometries and orientations. Upon actuation of the end effector 1102, the indexer 1118 may translate distally to engage the revolver 1114 by engaging the cams 1150 of the indexer 1118 against the cams 1126 of the revolver 1114.

Similar to the indexer 1118, the pusher 1120 may be operatively coupled to a drive input of a drive housing (e.g., one of the drive housings 206, 608 of FIGS. 2 and 6, respectively) such that, upon actuation, it is caused to move (e.g., reciprocate) within the bore 1113 to deploy a surgical clip 1108 from the revolver 1114 and into the opposed jaw members 1104,1106. The revolver 1114 may be configured to index such that a distal-most surgical clip 1108 becomes axially aligned with the pusher 1120 and is simultaneously placed in alignment with the opposed jaw members 1104, 1106. In the illustrated embodiment, the pusher 1120 may be configured to enter and translate distally through the indexer 1118 and the revolver 1114 to locate and apply an axial load on an aligned surgical clip 1108.

In the illustrated embodiment, the pusher 1120 includes a pusher shaft 1170 having a proximal end 1172a and a distal end 1172b. In some embodiments, the proximal end 1172a may extend to a drive housing where it may be operatively coupled to a drive input configured to actuate (longitudinally drive) the pusher 1120. In some embodiments, the pusher 1120 may be bifurcated at the distal end 1172b and thereby provide a pair of opposed pushing elements 1174,1176 that extend distally from the distal end 1172b. The pushing elements 1174,1176 may be generally aligned with the opposed jaw members 1104,1106, respectively.

The biasing member 1116 imparts a force on the revolver 1114 that helps facilitate repeated indexing of the revolver 1114 as it is alternatingly engaged and disengaged by the indexer 1118. In the illustrated embodiment, the biasing member 1116 is a spring 1160; however, it will be appreciated that the biasing member 1116 may instead comprise different materials or devices capable of providing a biasing force, without departing from the present disclosure. Here, the spring 1160 is provided in the distal region 1132b of the revolver compartment 1130, and arranged around the distal end 1124b of the revolver 1114. The spring 1160 extends between the annular flange 1122 and the guides 1128 and thus provides a passive biasing load on the revolver 1114 in the proximal direction.

The spring 1160 acts on the revolver 1114 to help facilitate rotation and indexing of the revolver 1114. More specifically, the spring 1160 biases the revolver 1114 proximally where its guides 1128 are fully engaged in the camming grooves 1136. When the indexer 1118 is distally translated, it engages and advances the revolver 1114 distally. The spring 1160 applies a counteracting force that maintains engagement of the camming surfaces 1126',1150' of the revolver 1114 and indexer 1118, respectively. As the revolver 1114 advances distally, engagement between the camming grooves 1136 and the guides inhibit rotation of the revolver 1114. However, once the guides 1128 exit the camming grooves 1136, the revolver 1114 is able to rotate (index) as the corresponding camming surfaces 1126',1150' slidably interact. The inclination (angle) of the camming surfaces 1126',1150' causes the revolver 1114 to simultaneously translate in a proximal direction such that the guides 1128 become angularly aligned with angularly adjacent camming grooves 1136. Once the revolver 1114 is properly indexed, a penultimate surgical clip 1108 becomes aligned with the opposed jaws 1104,1106 for deployment by the pusher 1120. As will be appreciated, this indexing action is similar in some respects to the operation of a click-action ballpoint pen.

Figure 12:
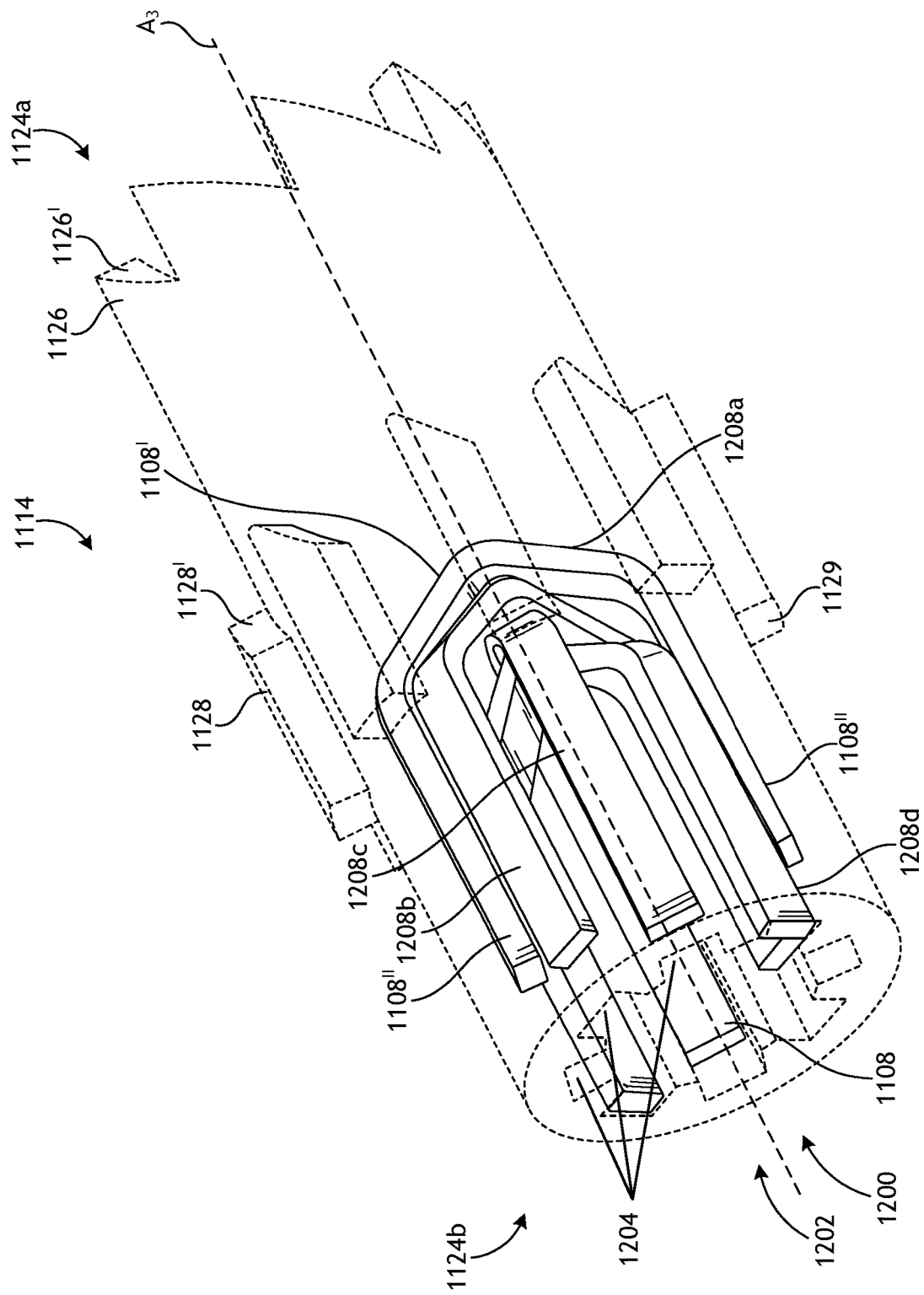
FIG. 12 is an enlarged isometric view of the revolver of the end effector of FIG. 11.

FIG. 12 is an enlarged isometric view of the revolver 1114, according to one or more embodiments. The revolver 1114 is hollow and includes an inner bore 1200 extending from the proximal end 1124a to the distal end 1124b thereof. As illustrated, the inner bore 1200 defines a clip chamber 1202 designed to hold/store the surgical clips 1108. The clip chamber 1202 also orients the surgical clips 1108 to be deployed legs 1108" first by the pusher 1120 (FIG. 11). Here, the clip chamber 1202 extends into the inner bore 1200 from the distal end 1124b. As will be appreciated, the distance that the clip chamber 1202 extends into the inner bore 1200 may depend on the length of the surgical clips 1108 and the number of surgical clips 1108 capable of being nested therein.

The clip chamber 1202 includes a plurality of clip slots 1204 defined into the inner surface of the inner bore 1200. Each clip slot 1204 may be configured to receive one leg of a given surgical clip 1108 and may be angularly opposite an opposing clip slot 1204 configured to receive the second leg of the given surgical clip 1108. Consequently, a pair of angularly opposite clips slots 1204 may be configured to receive and seat a single surgical clip 1108. In the illustrated embodiment, the clip chamber 1202 includes eight clip slots 1204 equidistantly spaced about the inner bore 1200 and therefore capable of receiving a corresponding four surgical clips 1108 stacked in a helical array. It will be appreciated, however, that more or less than four surgical clips 1108 may be accommodated within the revolver 1114 without departing from the present disclosure. The angular spacing and orientation of the clip slots 1204 helps the surgical clips 1108 to be arranged in a nested helical array, as illustrated.

As illustrated, the helically arrayed surgical clips 1108 are stacked (nested) one on top of the other from the proximal end 1124a towards the distal end 1124b. Here, the surgical clips 1108 include a proximal-most clip 1208a, a distal-most clip 1208d, and two intermediate clips 1208b,1208c. The surgical clips 1208a-d are arranged within the clips slots 1204 such that each surgical clip 1208a-d resides in a different radial plane relative to the longitudinal axis $A_3$ of the end effector 1102 (FIG. 1) and, therefore, the surgical clips are angularly offset from each other. In operation, the revolver 1114 may be rotated to align the distal-most clip 1208d with the opposed jaw members 1104,1106 for deployment. Following deployment of the distal-most clip 1208d, the end effector 1102 (FIG. 11) may be actuated again to rotate the revolver 1114 and thereby align the penultimate clip 1208c for deployment. This process may be repeated until the revolver 1114 is rotated to align the proximal-most clip 1208a with the jaw members 1104,1106 for deployment.

FIG. 12 also includes depicts the distal end 1129 of the guides 1128. As indicated above, the spring 1160 (FIG. 11) may be configured to engage the distal end 1129 of each guide 1128. In at least one embodiment, the distal end 1129 of each guide 1128 may be contoured and otherwise configured to receive the spring 1160 in a secure manner that inhibits slipping. However, in other embodiments, the distal ends 1129 may include different surface finishes or none at all.

Figure 13:
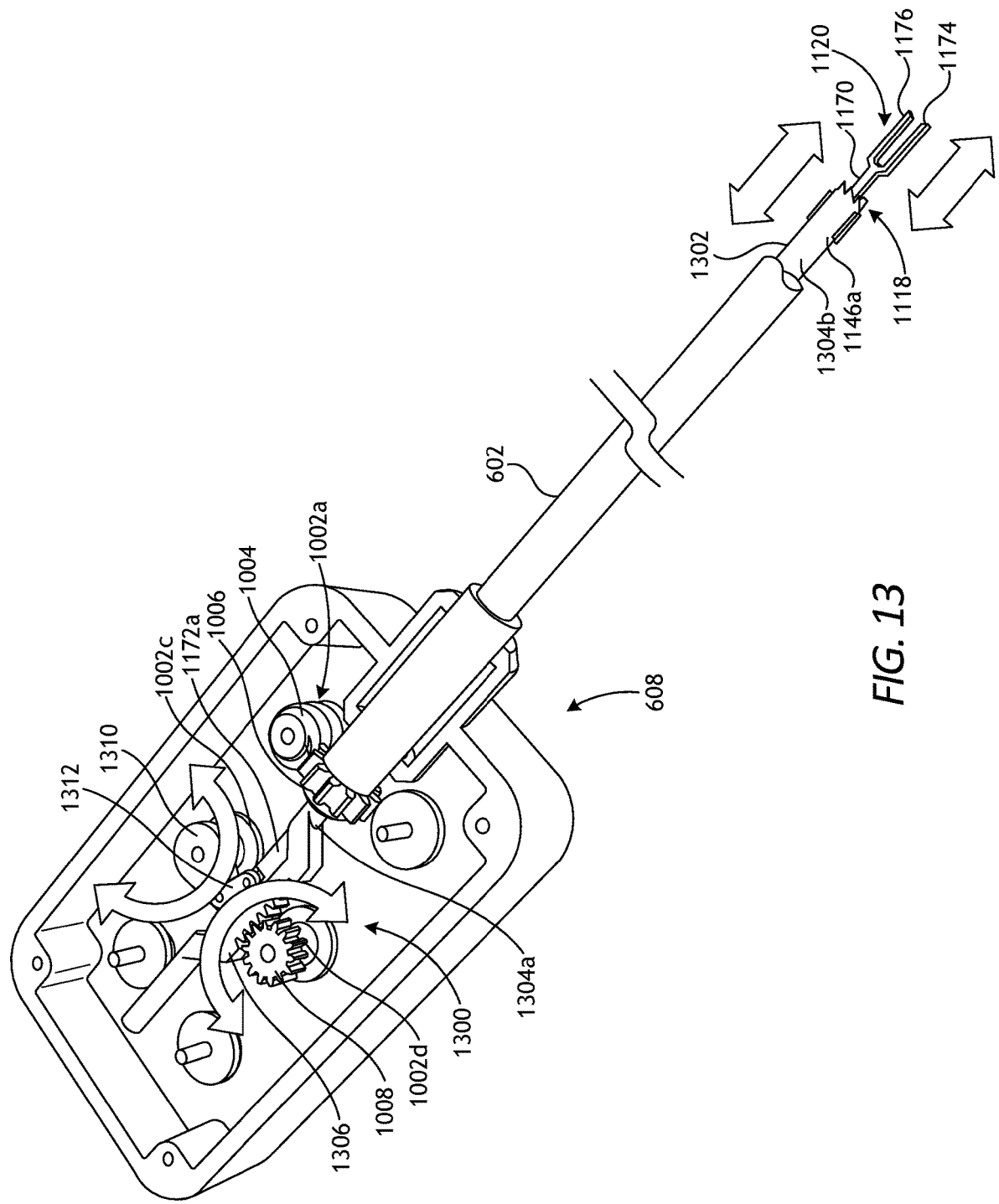
FIG. 13 is an isometric exposed view of the interior of the drive housing of the surgical tool of FIG. 11.

FIG. 13 is an isometric exposed view of the interior of an example embodiment of the drive housing 608, according to one or more embodiments. Various internal components of the drive housing 608 have been removed to view devices capable of actuating the indexer 1118 and the pusher 1120. In the illustrated embodiment, a linear actuator 1300 may be utilized to actuate the indexer 1118, which causes the revolver 1114 (FIGS. 11 and 12) to index (rotate).

As illustrated, the linear actuator 1300 may include a thrust shaft 1302 that includes a proximal end 1304a and a distal end 1304b. Here, the thrust shaft 1302 extends through the elongate shaft 602, with the proximal end 1304a extending into the drive housing 608 and the distal end 1304b being attached to the proximal end 1146a of the indexer 1118. While the indexer 1118 is described herein as being operatively coupled to the thrust shaft 1302, it is contemplated herein that the indexer 1118 may alternatively form an integral part or extension of the thrust shaft 1302, without departing from the scope of the disclosure.

The linear actuator 1300 may also include a rack gear 1306 attached to the proximal end 1304 of the thrust shaft 1302 and configured to mesh and interact with the spur gear 1008 operatively coupled to the fourth capstan 1002d. Accordingly, rotation of the spur gear 1008 (via actuation of the fourth drive input 906d of FIG. 9) will control the thrust shaft 1302 and thereby control indexing of the revolver 1114 (FIGS. 11 and 12). It will be appreciated, however, that the thrust shaft 1302 may be differently configured, for example to be actuated by any of the other capstans and corresponding drive inputs and/or with a different gearing assembly, without departing from the present disclosure.

The pusher 1120 may be actuated separately from the indexer 1118, or timed to deploy a surgical clip 1108 (FIGS. 11 and 12) after the revolver 1114 (FIGS. 11 and 12) has indexed the surgical clip 1108 into alignment with the opposed jaw members 1104,1106 (FIG. 11) as desired. In the illustrated embodiment, the thrust shaft 1302 is hollow and the pusher 1120 extends through the thrust shaft 1302, with the proximal end 1172a of the pusher shaft 1170 extending into the drive housing 608 and the distal end 1172b of the pusher shaft 1170 extending distally therefrom to a location proximate to the indexer 1118. In addition, a first link member 1310 is coupled to or forms part of the third capstan 1002c such that they rotate in unison. The first link member 1310 is coupled to a second link member 1312 that is configured to rotate relative to the first link member 1310. The second link member 1312 is coupled to the proximal end 1172a of the pusher shaft 1170 such that it may also rotate relative to the pusher shaft 1170, and thus interconnects the first link member 1310 and the proximal end 1172a of the pusher shaft 1170. Accordingly, rotation of the third capstan 1002c (via actuation of the third drive input 906c) will control linear movement of the pusher 1120 within the shaft 602 and thereby control loading of surgical clips 1108 into the opposed jaw members 1104,1106 as desired. It will be appreciated, however, that that the pusher 1120 may be differently configured, for example, to be actuated by any of the other capstans and corresponding drive inputs and/or with a gear arrangement in lieu of the linkage assembly, without departing from the present disclosure.

Figure 14A:
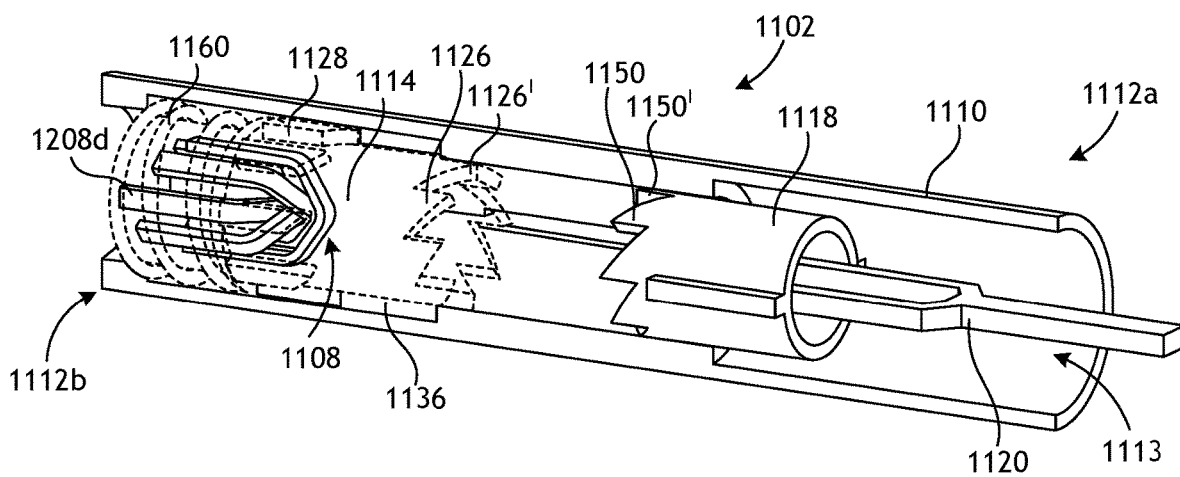
FIGS. 14A-14E are progressive exposed, partial isometric views of the end effector of FIG. 11 during example operation.

FIGS. 14A-14E are progressive isometric views of the end effector 1102 during example operation, according to one or more embodiments. FIG. 14A illustrates the end effector 1102 prior to actuation where the indexer 1118 and the pusher 1120 are retracted within the bore 1113 towards the proximal end 1112a of the body 1110. In this position, the revolver 1114 is fully seated within the camming grooves 1136 of the body 1110 and the spring 1160 biases the revolver 1114 proximally to enable the guides 1128 to be received within the camming grooves 1136. In the embodiment illustrated in FIG. 14A, it is assumed that the distal-most clip 1208d of the surgical clips 1108 is rotationally aligned with the opposed jaw members 1104,1106 (FIG. 14D) when the revolver 1114 is constrained in the camming grooves 1136, such that the pusher 1120 may deploy the distal-most clip 1108d before the revolver has indexed, as hereinafter described. However, in other embodiments, the distal-most clip 1208d is not rotationally aligned with the opposed jaw members 1104,1106 when the revolver 1112 is fully seated, but requires that the end effector 1102 be actuated to index the revolver 1114 to align the distal-most clip 1208d with the jaw members 1104,1106, before actuating the pusher 1120 to deploy the distal-most clip 1208d.

Figure 14B:
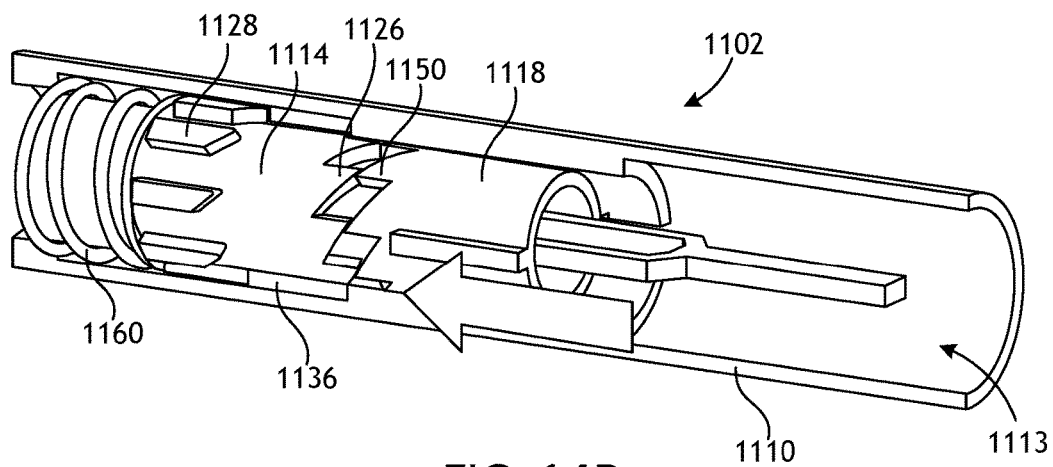
Figure 14C:
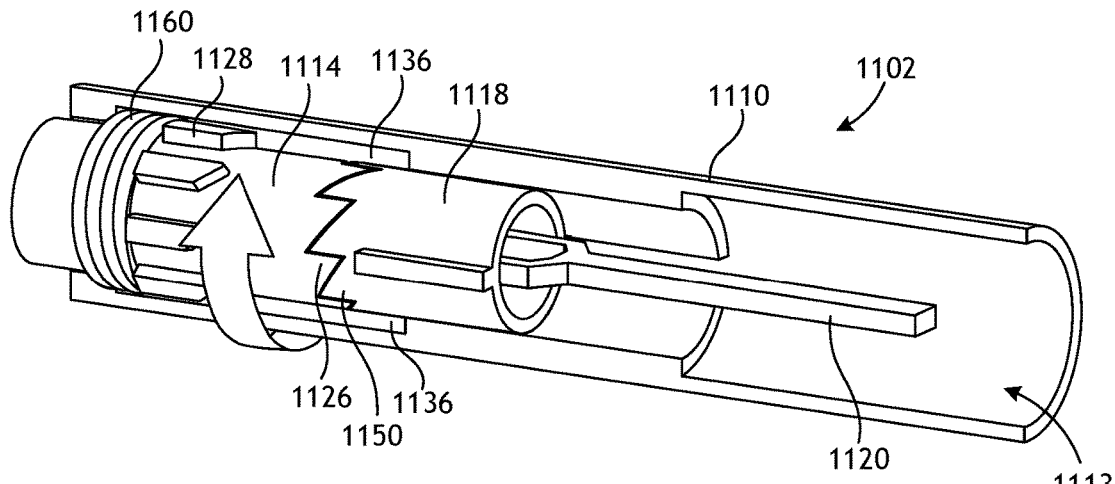
Figure 14D:
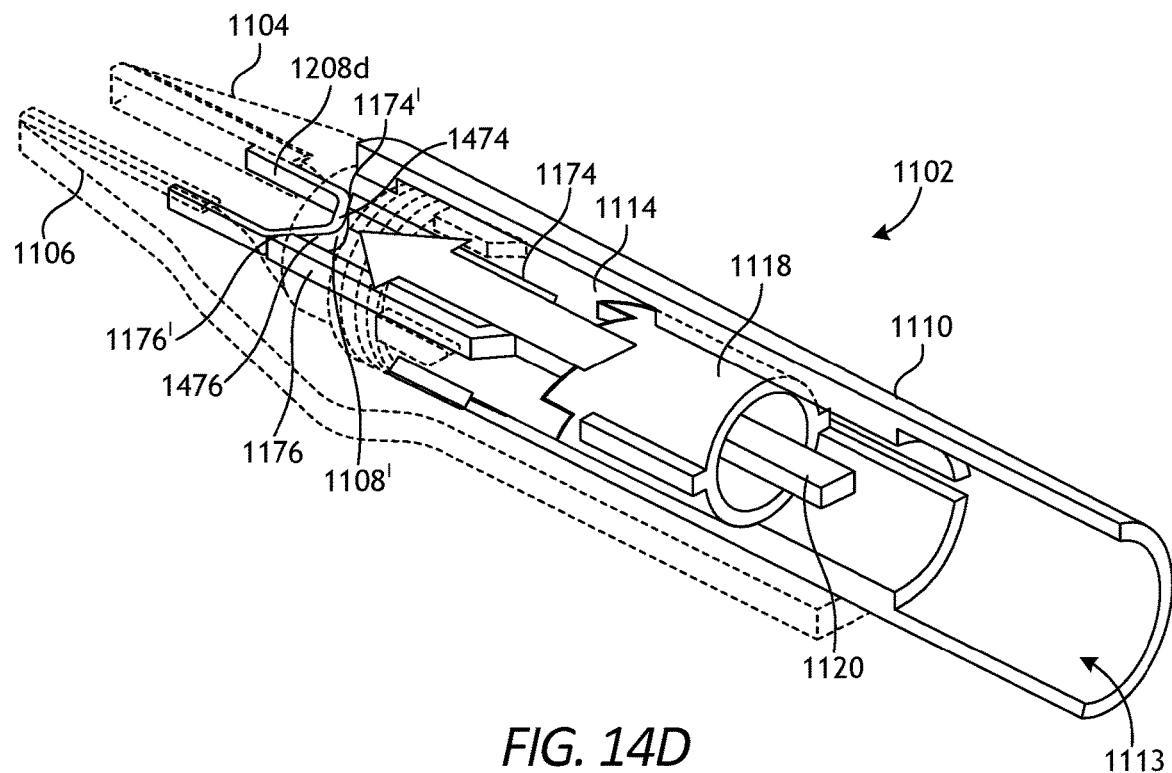

In FIG. 14B, the end effector 1102 is actuated to cause distal translation of the indexer 1118 to properly orient the distal-most surgical clip 1108 for deployment into the opposed jaw members 1104,1106 (FIG. 14D). Upon actuation, the indexer 1118 slides distally such that the cams 1150 make contact with the cams 1126 of the revolver 1114, which correspondingly drives the revolver 1114 distally and the guides 1128 of the revolver 1114 slide distally within the camming grooves 1136. Rotation of the revolver 1114 is inhibited when the guides 1128 are within the camming grooves 1136. In embodiments where the surgical clips 1108 align with the opposed jaws 1104,1106 when the revolver 1114 is constrained in the camming grooves 1136, the pusher 1120 may deploy the distal-most clip 1108d before the revolver 1114 is indexed. However, in embodiments where the distal-most clip 1208d is not rotationally aligned with the opposed jaws 1104,1106 when the revolver 1114 is constrained in the camming grooves 1136, the pusher 11120 deploys the distal-most surgical clip 1208d after the revolver 1114 is rotated.

In FIG. 14C, the revolver 1114 rotates to index the distal-most clip 1208d (FIG. 14D) into alignment with the opposed jaw members 1104,1106 (FIG. 14D) as the indexer 1118 continues to distally drive the revolver 1114. More specifically, the revolver 1114 may be able to rotate once the guides 1128 exit the camming grooves 1136 and the camming surface 1126' (FIG. 14A) of each cam 1126 is able to slidably engage the corresponding camming surfaces 1150' (FIG. 14A) of the cams 1150, which facilitates (urges) rotation of the revolver 1114. The revolver 1114 continues to rotate until the cams 1126 bottom out in the cams 1150. In embodiments where the distal-most clip 1208*d* is not rotationally aligned with the opposed jaw members 1104,1106 (FIG. 14D) when the revolver 1112 is seated within the camming grooves 1136, the distal-most clip 1208*d* will be in alignment with the opposed jaw members 1104,1106 and the pusher 1120 once the revolver 1114 finishes rotating. In other embodiments where the distal-most clip 1208*d* is rotationally aligned with the opposed jaw members 1104, 1106 (FIG. 14D) when the revolver 1112 is seated within the camming grooves 1136, the next distal-most surgical clip 1108 (e.g., the intermediate clip 1208*c*) will be in alignment the opposed jaw members 1104,1106 and the pusher 1120 once the revolver 1114 finishes rotating.

Once the distal-most clip 1208*d* is aligned with the opposed jaw members 1104,1106 (FIG. 14D), the pusher 1120 may be actuated to deploy the distal-most clip 1208*d*.

In FIG. 14D, the pusher 1120 is actuated distally and the pushing elements 1174,1176 are correspondingly moved to engage the aligned distal-most surgical clip 1208*d* at the crown 1108' thereof. The crown 1108' may include a pair of arms 1474,1476 configured to receive the corresponding pushing elements 1174,1176. Here, the arms 1474,1476 of the crown 1108' are angled and the pushing elements 1174, 1176 have contact surfaces 1174',1176' that are correspondingly angled and contoured to make complete contact therewith. It will be appreciated, however, that the crown 1108' may have various geometries and, therefore, that the contact surfaces 1174',1176' of the pusher 1120 may be contoured with various corresponding geometries. In addition, the contact surfaces 1174',1176' may include various features to inhibit slipping of the pushing elements 1174,1176 when engaging the crown 1108'. For example, the contact surfaces 1174',1176' may include barbs, ridges, and/or an elastomeric element that may increase friction when engaged with the surgical clips 1108.

Once the distal-most clip 1208*d* is deployed and positioned between the opposed jaw members 1104,1106, both the revolver 1114 and the indexer 1118 may be retracted proximally into the bore 1113 of the body 1110.

Figure 14E:
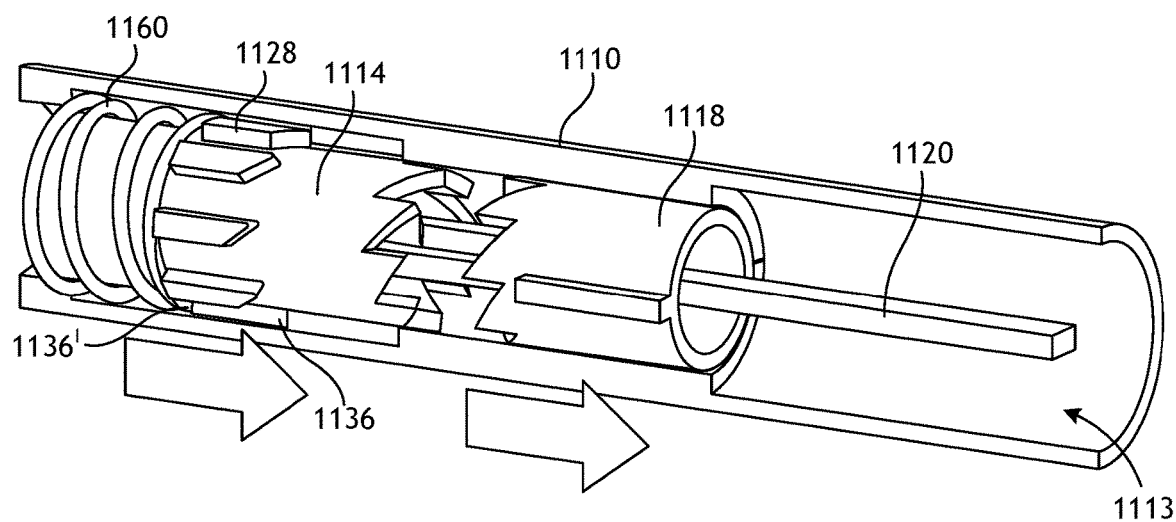

In FIG. 14E, the indexer 1118 is shown being retracted proximally into the bore 1113, which allows the spring 1160 to push the revolver 1114 proximally, and thereby causing the revolver 1114 to follow the indexer 1118 as it (i.e., the indexer 1118) translates proximally into the body 1110. Moreover, the guides 1128 of the revolver 1114 enter angularly adjacent camming grooves 1136 as the spring 1160 pushes the revolver 1114 proximally into the bore 1113. During this process, the camming surfaces 1128' of the guides 1128 slide upon the corresponding camming surfaces 1136' of the camming grooves 1136 to rotate the revolver 1114 so that the guides 1128 properly align with the angularly adjacent camming grooves 1136, and permits further axial translation of the revolver 1114.

Once the revolver 1114 rotates, the spring 1160 continues to proximally push the revolver 1114 until the revolver 1114 is seated within the body 1110 such that the guides 1128 are fully engaged in the appropriate camming grooves 1136. Seating the revolver 1114 in this position simultaneously places the penultimate clip 1208*c* into alignment with the opposed jaw members 1104,1106 (FIG. 14D) for deployment therein via subsequent actuation of the indexer 1118. In other embodiments, however, subsequent actuation of the indexer 1118 may be needed to rotate the penultimate clip 1208*c* into alignment with the opposed jaw members 1104, 1106 (FIG. 14D) prior to deployment via the pusher 1120. Also in the illustrated embodiment, the guides 1128 of the revolver 1114 are already rotated into alignment with the camming grooves 1136 of the body 1110 such that the spring 1160 may fully seat the guides 1128 into the camming grooves 1136 of the body 1110 without any obstruction and camming action between the guides 1128 and the camming grooves 1136. In other embodiments, however, additional camming action between the camming surfaces 1128' of the guides 1128 and the corresponding camming surfaces 1136' of the camming grooves 1136 facilitates fully seating the guides 1128 within the camming grooves 1136.

Figure 15:
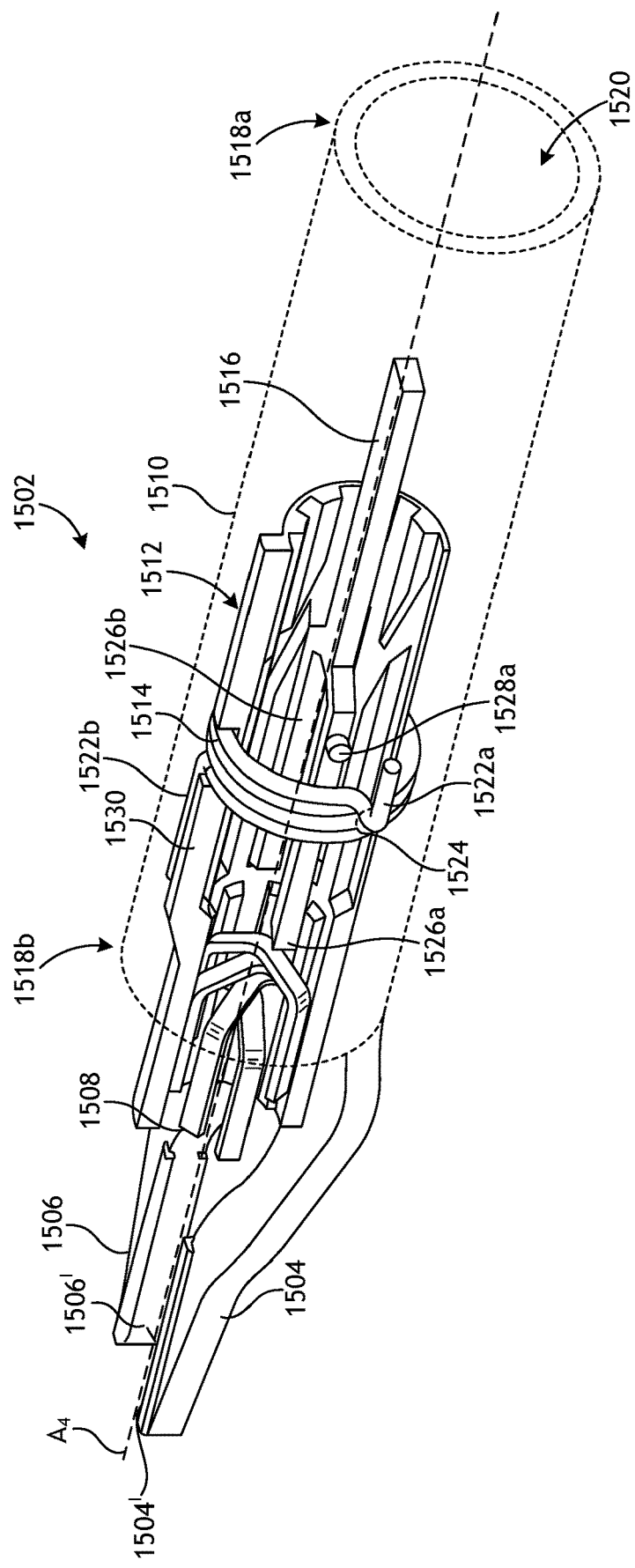
FIG. 15 is an enlarged isometric view of another example end effector.

FIG. 15 is an enlarged isometric view of another example end effector 1502, according to one or more embodiments of the present disclosure. The end effector 1502 may be similar in some respects to the end effector 1102 of FIG. 11, and thus may be incorporated into either or both of the surgical tools 200, 600 described herein above. Moreover, the end effector 1502 may comprise a clip applier having opposed jaw members 1504 and 1506 configured to collapse toward one another to crimp a surgical clip 1508 (four shown). As described herein, the end effector 1502 may incorporate various component parts and actuatable mechanisms or features that facilitate the feeding of the surgical clip 1508 into the opposed jaw members 1504,1506 and collapsing the opposed jaw members 1504,1506 to crimp the surgical clip 1508 when desired.

The end effector 1502 extends along a longitudinal axis $A_4$ and includes an elongate body 1510, a revolver 1512, a torsion member 1514, and a pusher 1516. The pusher 1516 may be longitudinally actuatable (movable) to index (rotate) the revolver 1512 and thereby selectively deploy the surgical clips 1508 housed within the revolver 1512. To accomplish this, the pusher 1516 may be operatively coupled to a drive input of a drive housing, such as one of the drive housings 206, 608 of FIGS. 2 and 6, respectively. In such embodiments, pusher 1516 may be operatively coupled to the second or third drive and driven gears 502*b,c*, 504*b,c* of FIG. 5 or one of the rotatable capstans 1002*b-f* of FIG. 10. The opposed jaw members 1504,1506 may each define a groove 1504',1506' that together define a path, slot, or track that the surgical clips 1508 travel as the pusher 1516 feeds them into interposition between the opposed jaw members 1504,1506 from the revolver 1512.

The body 1510 is generally cylindrical and includes a proximal end 1518*a* and a distal end 1518*b*. Moreover, the body 1510 defines a bore 1520 that extends between the proximal and distal ends 1518*a*,1518*b* and is sized to receive the revolver 1512 and the torsion member 1514 therein. The revolver 1512 may be adapted for rotation within the body 1510 and about the longitudinal axis $A_4$, as described below.

The torsion member 1514 may comprise a torsion spring that includes a first end 1522*a* and a second end 1522*b*, and may be configured to build/store mechanical energy when the first and second ends 1522*a*,1522*b* are twisted relative to each other. However, the torsion member 1514 may comprise other structures or materials in lieu of, or in addition to, the torsion spring, without departing from the present disclosure. As illustrated, the body 1510 defines an aperture 1524 through which the first end 1522*a* of the torsion member 1514 extends to enable the revolver 1512 to be "spring loaded" when installed within the bore 1520, as hereinafter described.

The pusher 1516 may be configured to longitudinally translate at least partially through the body 1510 and the revolver 1512 to selectively deploy the surgical clips 1508 into the opposed jaw members 1504,1506 as desired. Similar to the pusher 1120 of FIG. 11, the pusher 1516 is fork shaped and includes a pair of opposed pushing elements 1526a, 1526b that extend distally. The pushing elements 1526a, 1526b may be aligned with the opposed jaw members 1504,1506, respectively, and therefore may be capable of engaging and distally moving the surgical clips 1508 into interposition therebetween.

The pusher 1516 may be actuated to distally drive one of the surgical clips 1508 into the opposed jaw members 1504,1506. In some embodiments, the pusher 1516 is operatively coupled to one or more of the capstans 1002b-f within the drive housing 608 (FIGS. 6 and 13). For example, the pusher 1516 may include a shaft that extends proximally through the elongate shaft 602 and is coupled to one or more of the capstans 1002 within the drive housing 608 via a linkage assembly or rack and pinion interface. In one embodiment, the shaft of the pusher 1516 extends into the drive housing 608 and is coupled to the rack gear 1306 that is configured to mesh and interact with the spur gear 1008 operatively coupled to the fourth capstan 1002d (FIGS. 6 and 13). In another embodiment, the shaft of the pusher 1516 extends into the drive housing 608 and is operatively coupled to the third capstan 1002c via the first link member 1310 and the second link member 1312 (FIGS. 6 and 13). However, the pusher 1516 may be differently reciprocated without departing from the present disclosure.

The pusher 1516 further includes one or more features that may help guide the pusher 1516 within the revolver 1512. In the illustrated embodiment, the pusher 1516 includes a pair of opposed studs 1528a and 1528b (obscured from view) that extend laterally from the opposed pushing elements 1526a,1526b, respectively. It will be appreciated that more or less than the pair of studs 1528a,1528b may be utilized, without departing from the present disclosure. Moreover, it will be appreciated that the pair of studs 1528a,1528b (or any of them) may include different geometries and/or be differently arranged on the pusher 1516 without departing from the present disclosure.

Figure 16:
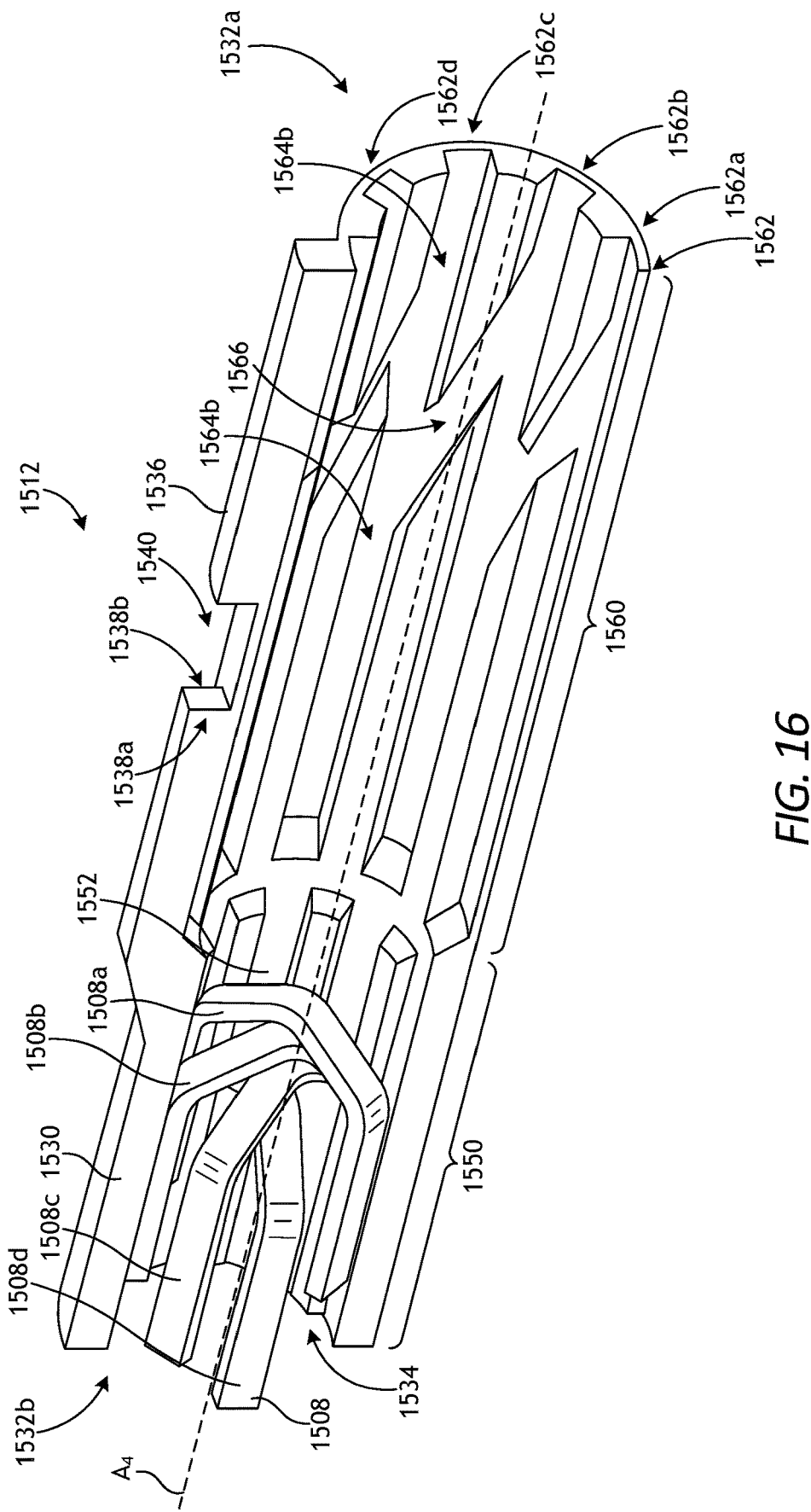
FIG. 16 is an exposed, partial cross-sectional side view of the revolver of the end effector of FIG. 15.

FIG. 16 is an enlarged isometric cross-sectional view of the revolver 1512, according to one or more embodiments of the present disclosure. As illustrated, the revolver 1512 comprises a revolver body 1530 that has an open proximal end 1532a, an open distal end 1532b, and a bore 1534 extending therebetween. The revolver body 1530 may be cylindrically shaped and sized to be received within the body 1510 (FIG. 15). In other embodiments, however, the revolver body 1530 may include other geometries, without departing from the present disclosure. In some embodiments, the revolver 1512 is disposed within the body 1510 with the open distal end 1532b extending past the distal end 1518b (FIG. 15) of the body 1510 and arranged proximate to the opposed jaw member 1504,1506. In other embodiments, however, the open distal end 1532b may be arranged within the body 1510 and otherwise proximal to the distal end 1518b of the body 1510.

The revolver 1512 includes a detent or spline 1536 configured to receive and abut the second end 1522b (FIG. 15) of the torsion member 1514 (FIG. 15) such that the torsion member 1514 is able to retain tension when its first and second ends 1522a,1522b are twisted. Accordingly, the torsion member 1514 imparts a constant torsion load on the revolver 1512 when twisted out of an equilibrium position, thereby urging the revolver 1512 to rotate about the longitudinal axis $A_4$.

In the illustrated embodiment, the spline 1536 is provided or otherwise defined on the revolver 1114 and arranged to abut the second end 1522b of the torsion member 1514. Here, the spline 1536 extends radially from the revolver body 1530 and includes a front face 1538a and rear face 1538b. In addition, the spline 1536 defines a recess 1540 that allows the torsion member 1514 to extend around the spline 1536 such that the second end 1522b thereof may abut the rear face 1538b. Thus, the torsion member 1514 may retain tension when impinged between the aperture 1524 (FIG. 15) of the body 1510 (FIG. 15) and the spline 1536 of the revolver 1512. Moreover, the spline 1536 extends substantially parallel to the longitudinal axis $A_4$.

The revolver 1512 includes a plurality of discrete regions arranged within the bore 1534. As illustrated, a clip region 1550 is formed within the bore 1534 and configured to receive one or more of the surgical clips 1508. In operation, the surgical clips 1508 are stacked within the clip region 1550 in a nested helical array. The clip region 1550 defines a plurality of clip slots 1552 defined into the inner surface of the bore 1534. Each clip slot 1552 may be configured to receive one leg of a given surgical clip 1508 and may be angularly opposite an opposing clip slot 1504 configured to receive the second leg of the given surgical clip 1508. Consequently, a pair of angularly opposite clips slots 1552 may be configured to receive and seat a single surgical clip 1508. In the illustrated embodiment, the clip region 1550 includes eight clip slots 1552 equidistantly spaced about the bore 1534 and thereby capable of receiving a corresponding four surgical clips 1508 stacked in a helical array. It will be appreciated, however, that more or less than four surgical clips 1508 may be housed within the revolver 1512 without departing from the present disclosure. The angular spacing and orientation of the clip slots 1552 helps the surgical clips 1508 to be arranged in a nested helical array, as illustrated.

In the illustrated example, the surgical clips 1508 include a proximal-most clip 1508a, a pair of intermediate clips 1508b,1508c, and a distal-most surgical clip 1508d. To load the revolver 1512, the proximal-most clip 1508a is first inserted into a first pair of clip slots 1552. The first intermediate clip 1508b is then inserted into a second pair of clip slots 1552 angularly offset from the first pair of clip slots 1552, the second intermediate clip 1508c is inserted into a third pair of clip slots 1552 angularly offset from the second pair of clip slots 1552, and the distal-most surgical clip 1508d is inserted into a fourth pair of clip slots 1552 angularly offset from the third pair of clip slots 1552. Thus, the clip slots 1552 orient the surgical clips 1508a-1508d in a helical array when stacked/stored within the clip region 1550. It will be appreciated, however, that the clip region 1550 may be differently configured with more or less clip slots 1552 to house any number of the surgical clips 1508 in various orientations without departing from the present disclosure.

The revolver 1512 also includes a biasing region 1560 configured to guide the pusher 1516 (FIG. 15). The biasing region 1560 extends into the bore 1534 at the open proximal end 1532a and terminates at or near the clip region 1550. As hereinafter described, the pusher 1516 may be configured to engage the biasing region 1560 and help index the revolver 1512 as it traverses the biasing region 1560.

As illustrated, the biasing region 1560 includes a plurality of biasing grooves 1562 (referred to hereinafter as a "plurality of grooves") configured to receive and guide the pusher 1516 (FIG. 15) as it reciprocates distally and proximally within the bore 1534. Each angularly opposite pair of the grooves 1562 may be axially aligned with a corresponding angularly opposite pair of the clip slots 1552 of the clip region 1550. The studs 1528a,1528b (FIG. 15) of the pusher 1516 may be configured to selectively and sequentially traverse within each pair of the grooves 1562 so that the pushing elements 1526a,1526b are aligned to drive each surgical clip 1508 into the opposed jaw members 1504,1506. The illustrated embodiment includes four pairs of grooves 1562 that each correspond with one of the four pairs of clip slots 1552. In other embodiments, however, more or less than four pairs of grooves 1562 (and corresponding pairs of clip slots 1552) may be utilized.

Each of the pairs of grooves 1562 includes a proximal portion 1564a, a distal portion 1564b, and a connecting channel 1566 that interconnects the proximal and distal portions 1564a,1564b of each groove 1562 and thereby provides a pathway that connects each groove 1562 to an angularly adjacent (neighboring) groove 1562. The proximal portion 1564a, the distal portion 1564b, and the connecting channel 1566 are each arranged to slidably receive the studs 1528a,1528b (FIG. 15) of the pusher 1516, which in turn rotates the revolver 1512 within the body 1510 as the pusher 1516 traverses the groove 1562. Thus, the connecting channel 1566 connect angularly adjacent pairs of grooves 1562 and facilitate rotation of the revolver 1512 when the studs 1528a,1528b travel into the angularly adjacent pair of grooves 1562.

In the illustrated embodiment, the pairs of grooves 1562 include a first pair of grooves 1562a, a second pair of grooves 1562b, a third pair of grooves 1562c, and a fourth pair of grooves 1562d. Here, a first of the connecting channels 1566 connects the first pair of grooves 1562a to its neighboring second and fourth pairs of grooves 1562b, 1562d; a second of the connecting channels 1566 connects the second pair of grooves 1562b to its neighboring first and third pairs of grooves 1562a,1562c; a third of the connecting channels 1566 connects the third pair of grooves 1562c to its neighboring second and fourth pairs of grooves 1562b, 1562d; and a fourth of the connecting channels 1566 connects the fourth pair of grooves 1562d to its neighboring third and first pairs of grooves 1562c,1562a.

The revolver 1512 is constantly biased to rotate in an attempt to relieve the torsional load (spring force) built up in the torsion member 1514. As the pusher 1516 advances distally, the studs 1528a,1528b are able to bypass (traverse) the connecting channels 1566 in the distal direction and, therefore, remain in the same pair of grooves 1562 to thereby engage the distal-most surgical clip 1508d and discharge it from the revolver 1512. However, upon retracting the pusher 1516 in the proximal direction, the torsional load provided by the torsion member 1514 forces the studs 1528a,1528b to enter and follow the connecting channels 1566, which allows the revolver 1512 to rotate and place the studs 1528a,1528b in the angularly adjacent pair of grooves 1562. Allowing the revolver 1512 to rotate where the studs 1528a,1528b are positioned in the angularly adjacent pair of grooves 1562 simultaneously aligns the penultimate surgical clip 1508 with the pusher 1516. This process is repeated to discharge the penultimate surgical clip 1508 from the revolver 1512.

Figure 17A:
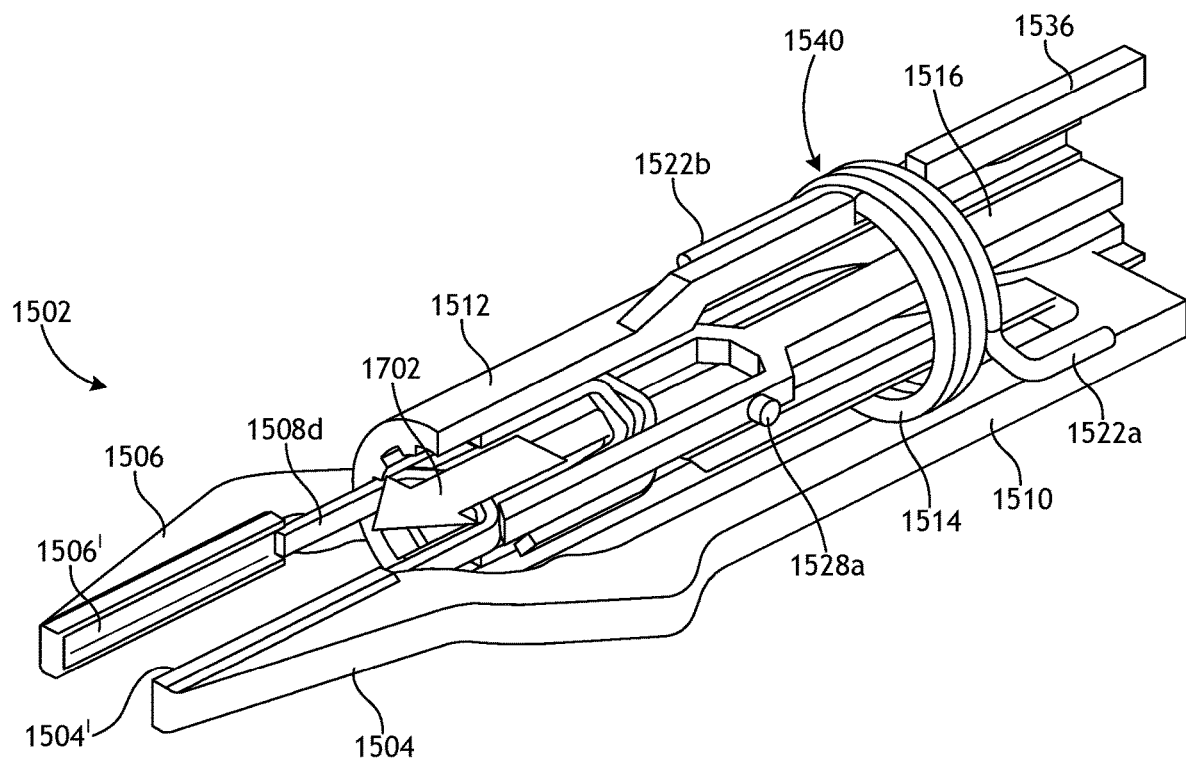
FIGS. 17A-17B are progressive exposed, partial isometric views of the end effector of FIG. 15 during an example reloading operation.
Figure 17B:
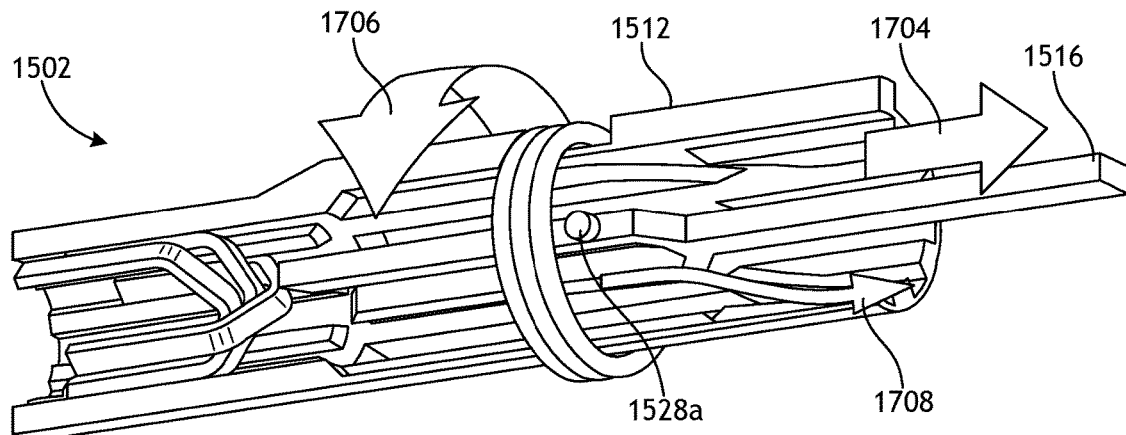

FIGS. 17A-17B are isometric views of the end effector 1502 showing example operation, according to one or more embodiments of the present disclosure. In FIG. 17A, the pusher 1516 is shown being moved in a distal direction 1702 to engage and drive the distal-most surgical clip 1508d from its respective clip slot 1552 (FIG. 16) within the revolver 1512 and into the grooves 1504',1506' defined in the opposed jaw members 1504,1506. While not fully illustrated, the studs 1528a,1528b of the pusher 1516 are engaged within the distal portion 1564b (FIG. 16) of the groove 1562 (FIG. 16) that are aligned with the grooves 1504',1506' (e.g., the third pair of grooves 1562c of FIG. 16).

FIG. 17B illustrates the pusher 1516 as it moves in a proximal direction 1704 relative to the revolver 1512. Moving the pusher 1516 in the proximal direction 1704 allows the revolver 1512 to index or rotate in a counter-clockwise direction 1706. More specifically, the torsion member 1514 is installed in the end effector 1502 and twisted to build up a torsional load that continuously biases the revolver 1512 in the counter-clockwise direction 1706. Rotation of the revolver 1512 is constrained when the studs 1528a,1528b of the pusher 1516 are engaged within the distal portion 1564b of the groove 1562 (e.g., the third pair of grooves 1562c (FIG. 16)). Once the pusher 1516 moves in the proximal direction 1704 a sufficient distance such the studs 1528a, 1528b (FIG. 17A) are no longer engaged within the distal portion 1564b thereof, rotation of the revolver 1512 is no longer inhibited and the torsion member 1514 rotates the revolver 1512 in the counter-clockwise direction 1706 such that the studs 1528a,1528b enter the connecting channels 1566. The connecting channels 1566 direct the studs 1528a, 1528b in a downward path 1708 so that they enter the proximal portion 1564a of the angularly adjacent pair of grooves 1562 (e.g., the second pair of grooves 1562b (FIG. 16)), which simultaneously aligns the penultimate surgical clip 1508 with the pusher 1516. The pusher 1516 may then advance distally in the angularly adjacent pair of grooves 1562, with the studs 1528a,1528b bypassing (traversing) the connecting channels 1566 and remaining in the same pair of grooves 1562, to engage the penultimate surgical clip 1508 and discharge it from the revolver 1512. This process may be repeated to discharge the next penultimate surgical clip 1508 from the revolver 1512.

Embodiments disclosed herein include:

A. An end effector for a surgical clip applier that includes an elongate body, a clip revolver rotatably positioned within the elongate body and providing an inner bore that defines a plurality of clip slots angularly spaced from each other about an inner surface of the inner bore, wherein a plurality of surgical clips are receivable within the plurality of clip slots in a nested helical array, a clip advancer longitudinally movable within the elongate body and selectively engageable with each surgical clip based on rotation of the clip revolver, and first and second jaw members extending past a distal end of the elongate body and aligned to receive axially-aligned surgical clips from the clip revolver as the clip advancer advances distally, wherein the clip revolver is rotatable to sequentially align each surgical clip with the first and second jaw members.

B. A method of operating an end effector of a surgical clip applier that includes positioning the end effector adjacent a patient for operation, the end effector including an elongate body, a clip revolver rotatably positioned within the elongate body and providing an inner bore that defines a plurality of clip slots angularly spaced from each other about an inner surface of the inner bore, a plurality of surgical clips arranged within the plurality of clip slots in a nested helical array, a clip advancer longitudinally movable within the elongate body, and first and second jaw members extending past a distal end of the elongate body. The method further including distally advancing the clip advancer to engage a distal-most surgical clip of the plurality of surgical clips, distally advancing the distal-most surgical clip out of the clip revolver and into interposition between the first and second jaw members with the clip advancer, and collapsing the first and second jaw members to crimp the distal-most surgical clip.

C. A surgical clip applier that includes a drive housing, an elongate shaft that extends from the drive housing, and an end effector arranged at a distal end of the elongate shaft, the end effector including an elongate body, a clip revolver rotatably positioned within the elongate body and providing an inner bore that defines a plurality of clip slots angularly spaced from each other about an inner surface of the inner bore, wherein a plurality of surgical clips are receivable within the plurality of clip slots in a nested helical array, a clip advancer longitudinally movable within the elongate body and selectively engageable with each surgical clip based on rotation of the clip revolver, and first and second jaw members extending past a distal end of the elongate body and aligned to receive axially-aligned surgical clips from the clip revolver as the clip advancer advances distally, wherein the clip revolver is rotatable to sequentially align each surgical clip with the first and second jaw members.

Each of embodiments A, B, and C may have one or more of the following additional elements in any combination: Element 1: further comprising an indexer longitudinally movable within the elongate body and engageable with the clip revolver to rotate the clip revolver. Element 2: wherein the indexer includes one or more rails that are received within one or more corresponding guides provided in an inner surface of the elongate body. Element 3: wherein a camming surface of the indexer is engageable with a corresponding camming surface of the clip revolver to rotate the clip revolver. Element 4: further comprising a plurality of axially-extending camming grooves provided on an inner radial surface of the body, and a plurality of guides extending radially from an outer surface of the clip revolver and receivable within the plurality of camming grooves. Element 5: further comprising a biasing member arranged within the body to bias the plurality of guides into the plurality of camming grooves. Element 6: further comprising a torsion member operatively coupled to the elongate body and the clip revolver and imparting a torsional load on the clip revolver that urges the clip revolver to rotate relative to the elongate body, a plurality of axially-extending grooves defined on the inner bore of the clip revolver, one or more studs extending laterally from the clip advancer and receivable within the plurality of axially-extending grooves to prevent the clip revolver from rotating, and a channel groove that interconnects angularly adjacent axially-extending grooves of the plurality of axially-extending grooves. Element 7: wherein the one or more studs bypass the channel groove as the clip advancer advances distally within a given axially-extending groove of the plurality of axially-extending grooves, wherein the one or more studs are received within the channel groove as the clip advancer retracts proximally within the given axially-extending groove, and wherein the torsional load rotates the clip revolver and forces the one or more studs to enter and follow an angularly adjacent axially-extending groove of the plurality of axially-extending grooves. Element 8: wherein the plurality of clip slots forms pairs of angularly opposite clip slots, and each pair of angularly opposite clip slots receives a corresponding one of the plurality of surgical clips, and wherein the plurality of surgical clips are receivable within the pairs of clip slots such that each surgical clip resides in a different radial plane relative to a longitudinal axis of the end effector. Element 9: wherein the plurality of surgical clips are angularly offset from each other within the pairs of clips slots, and wherein the revolver is rotatable to sequentially align the pairs of clips slots with the first and second jaw members. Element 10: wherein the plurality of surgical clips are receivable within the plurality of clip slots such that a crown of more proximal surgical clips are stacked upon a crown of more distal surgical clips, and legs of the more proximal surgical clips extend past the crown of the more distal surgical clips.

Element 11: further comprising rotating the clip revolver from a first position to a second position where a penultimate surgical clip of the plurality of surgical clips aligns with the first and second jaw members. Element 12: wherein a plurality of guides extend radially from an outer surface of the clip revolver and a plurality of axially-extending camming grooves are provided in an inner radial surface of the elongate body, the method further comprising maintaining the clip revolver in the first position by biasing the plurality of guides into the plurality of axially-extending camming grooves, and distally advancing the clip revolver such that the plurality of guides exit the plurality of camming grooves and thereby allow the clip revolver to rotate from the first position to the second position. Element 13: wherein the end effector further includes a torsion member operatively coupled to the elongate body and the clip revolver, a plurality of axially-extending grooves defined on the inner bore of the clip revolver, and a channel groove that interconnects angularly adjacent axially-extending grooves of the plurality of axially-extending grooves, the method further comprising imparting a torsional load on the clip revolver with the torsion member and thereby urging the clip revolver to rotate away from the first position, and maintaining the clip revolver in the first position with one or more studs extending laterally from the clip advancer and received within the plurality of axially-extending grooves. Element 14: further comprising when the revolver is in the first position, bypassing the channel groove with the one or more studs as the clip advancer advances distally within a given axially-extending groove of the plurality of axially-extending grooves, receiving the one or more studs within the channel groove as the clip advancer retracts proximally within the given axially-extending groove, rotating the clip revolver to the second position with the torsional load once the one or more studs enter the channel groove, and receiving the one or more studs within an angularly adjacent axially-extending groove of the plurality of axially-extending grooves. Element 15: further comprising distally advancing the penultimate surgical clip out of the clip revolver and into interposition between the first and second jaw members, and collapsing the first and second jaw members to crimp the penultimate surgical clip.

Element 16: further comprising an articulable wrist joint interposing the end effector and the elongate shaft. Element 17: wherein the plurality of clip slots forms pairs of angularly opposite clip slots, and each pair of angularly opposite clip slots receives a corresponding one of the plurality of surgical clips, and wherein the plurality of surgical clips are receivable within the pairs of clip slots such that each surgical clip resides in a different radial plane relative to a longitudinal axis of the end effector.

By way of non-limiting example, exemplary combinations applicable to A, B, and C include: Element 1 with Element 2; Element 1 with Element 3; Element 3 with Element 4; Element 4 with Element 5; Element 6 with Element 7; Element 8 with Element 9; Element 8 with Element 10; Element 11 with Element 12; Element 11 with Element 13; and Element 14 with Element 15.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. An end effector for a surgical clip applier, comprising:
   an elongate body;
   a clip revolver rotatably positioned within the elongate body and providing an inner bore that defines a plurality of clip slots angularly spaced from each other about an inner surface of the inner bore, wherein a plurality of surgical clips are receivable within the plurality of clip slots in a nested helical array;
   a clip advancer longitudinally movable within the elongate body and selectively engageable with each surgical clip based on rotation of the clip revolver; and
   first and second jaw members extending past a distal end of the elongate body and aligned to receive axially-aligned surgical clips from the clip revolver as the clip advancer advances distally, wherein the clip revolver is rotatable to sequentially align each surgical clip with the first and second jaw members.

2. The end effector of claim 1, further comprising an indexer longitudinally movable within the elongate body and engageable with the clip revolver to rotate the clip revolver.

3. The end effector of claim 2, wherein the indexer includes one or more rails that are received within one or more corresponding guides provided in an inner surface of the elongate body.

4. The end effector of claim 2, wherein a camming surface of the indexer is engageable with a corresponding camming surface of the clip revolver to rotate the clip revolver.

5. The end effector of claim 4, further comprising:
   a plurality of axially-extending camming grooves provided on an inner radial surface of the elongate body; and
   a plurality of guides extending radially from an outer surface of the clip revolver and receivable within the plurality of camming grooves.

6. The end effector of claim 5, further comprising a biasing member arranged within the elongate body to bias the plurality of guides into the plurality of camming grooves.

7. The end effector of claim 1, further comprising:
   a torsion member operatively coupled to the elongate body and the clip revolver and imparting a torsional load on the clip revolver that urges the clip revolver to rotate relative to the elongate body;
   a plurality of axially-extending grooves defined on the inner bore of the clip revolver;
   one or more studs extending laterally from the clip advancer and receivable within the plurality of axially-extending grooves to prevent the clip revolver from rotating; and
   a channel groove that interconnects angularly adjacent axially-extending grooves of the plurality of axially-extending grooves.

8. The end effector of claim 7, wherein the one or more studs bypass the channel groove as the clip advancer advances distally within a given axially-extending groove of the plurality of axially-extending grooves,
   wherein the one or more studs are received within the channel groove as the clip advancer retracts proximally within the given axially-extending groove, and
   wherein the torsional load rotates the clip revolver and forces the one or more studs to enter and follow an angularly adjacent axially-extending groove of the plurality of axially-extending grooves.

9. The end effector of claim 1, wherein the plurality of clip slots forms pairs of angularly opposite clip slots, and each pair of angularly opposite clip slots receives a corresponding one of the plurality of surgical clips, and wherein the plurality of surgical clips are receivable within the pairs of clip slots such that each surgical clip resides in a different radial plane relative to a longitudinal axis of the end effector.

10. The end effector of claim 9, wherein the plurality of surgical clips are angularly offset from each other within the pairs of clips slots, and wherein the revolver is rotatable to sequentially align the pairs of clips slots with the first and second jaw members.

11. The end effector of claim 9, wherein the plurality of surgical clips are receivable within the plurality of clip slots such that a crown of more proximal surgical clips are stacked upon a crown of more distal surgical clips, and legs of the more proximal surgical clips extend past the crown of the more distal surgical clips.

12. A method of operating an end effector of a surgical clip applier, comprising:

positioning the end effector adjacent a patient for operation, the end effector including:
- an elongate body;
- a clip revolver rotatably positioned within the elongate body and providing an inner bore that defines a plurality of clip slots angularly spaced from each other about an inner surface of the inner bore;
- a plurality of surgical clips arranged within the plurality of clip slots in a nested helical array;
- a clip advancer longitudinally movable within the elongate body; and
- first and second jaw members extending past a distal end of the elongate body;

distally advancing the clip advancer to engage a distal-most surgical clip of the plurality of surgical clips;

distally advancing the distal-most surgical clip out of the clip revolver and into interposition between the first and second jaw members with the clip advancer; and collapsing the first and second jaw members to crimp the distal-most surgical clip.

13. The method of claim 12, further comprising rotating the clip revolver from a first position to a second position where a penultimate surgical clip of the plurality of surgical clips aligns with the first and second jaw members.

14. The method of claim 13, wherein a plurality of guides extend radially from an outer surface of the clip revolver and a plurality of axially-extending camming grooves are provided in an inner radial surface of the elongate body, the method further comprising:
- maintaining the clip revolver in the first position by biasing the plurality of guides into the plurality of axially-extending camming grooves; and
- distally advancing the clip revolver such that the plurality of guides exit the plurality of camming grooves and thereby allow the clip revolver to rotate from the first position to the second position.

15. The method of claim 13, wherein the end effector further includes a torsion member operatively coupled to the elongate body and the clip revolver, a plurality of axially-extending grooves defined on the inner bore of the clip revolver, and a channel groove that interconnects angularly adjacent axially-extending grooves of the plurality of axially-extending grooves, the method further comprising:
- imparting a torsional load on the clip revolver with the torsion member and thereby urging the clip revolver to rotate away from the first position; and
- maintaining the clip revolver in the first position with one or more studs extending laterally from the clip advancer and received within the plurality of axially-extending grooves.

16. The method of claim 15, further comprising:
- when the revolver is in the first position, bypassing the channel groove with the one or more studs as the clip advancer advances distally within a given axially-extending groove of the plurality of axially-extending grooves;
- receiving the one or more studs within the channel groove as the clip advancer retracts proximally within the given axially-extending groove;
- rotating the clip revolver to the second position with the torsional load once the one or more studs enter the channel groove; and
- receiving the one or more studs within an angularly adjacent axially-extending groove of the plurality of axially-extending grooves.

17. The method of claim 12, further comprising:
- distally advancing the penultimate surgical clip out of the clip revolver and into interposition between the first and second jaw members; and
- collapsing the first and second jaw members to crimp the penultimate surgical clip.

18. A surgical clip applier, comprising:
- a drive housing;
- an elongate shaft that extends from the drive housing; and
- an end effector arranged at a distal end of the elongate shaft, the end effector including:
  - an elongate body;
  - a clip revolver rotatably positioned within the elongate body and providing an inner bore that defines a plurality of clip slots angularly spaced from each other about an inner surface of the inner bore, wherein a plurality of surgical clips are receivable within the plurality of clip slots in a nested helical array;
  - a clip advancer longitudinally movable within the elongate body and selectively engageable with each surgical clip based on rotation of the clip revolver; and
  - first and second jaw members extending past a distal end of the elongate body and aligned to receive axially-aligned surgical clips from the clip revolver as the clip advancer advances distally, wherein the clip revolver is rotatable to sequentially align each surgical clip with the first and second jaw members.

19. The surgical clip applier of claim 18, further comprising an articulable wrist joint interposing the end effector and the elongate shaft.

20. The surgical clip applier of claim 18, wherein the plurality of clip slots forms pairs of angularly opposite clip slots, and each pair of angularly opposite clip slots receives a corresponding one of the plurality of surgical clips, and wherein the plurality of surgical clips are receivable within the pairs of clip slots such that each surgical clip resides in a different radial plane relative to a longitudinal axis of the end effector.

* * * * *